US011432877B2

(12) United States Patent
Nash et al.

(10) Patent No.: US 11,432,877 B2
(45) Date of Patent: Sep. 6, 2022

(54) SURGICAL FIELD CAMERA SYSTEM THAT ONLY USES IMAGES FROM CAMERAS WITH AN UNOBSTRUCTED SIGHT LINE FOR TRACKING

(71) Applicant: MedTech S.A., Montpellier (FR)

(72) Inventors: Seth Anderson Nash, Fort Wayne, IN (US); Pierre Couture, Montreal (CA)

(73) Assignee: MedTech S.A., Montpellier (FR)

( * ) Notice: Subject to any disclaimer, the term of this patent is extended or adjusted under 35 U.S.C. 154(b) by 480 days.

(21) Appl. No.: 16/040,951

(22) Filed: Jul. 20, 2018

(65) Prior Publication Data

US 2019/0038362 A1    Feb. 7, 2019

Related U.S. Application Data

(60) Provisional application No. 62/540,207, filed on Aug. 2, 2017, provisional application No. 62/616,264, filed on Jan. 11, 2018.

(51) Int. Cl.
*A61B 34/20* (2016.01)
*G06T 19/00* (2011.01)
(Continued)

(52) U.S. Cl.
CPC .............. *A61B 34/20* (2016.02); *A61B 34/10* (2016.02); *A61B 34/25* (2016.02); *A61B 90/36* (2016.02);
(Continued)

(58) Field of Classification Search
CPC ......... A61B 34/20; A61B 34/25; A61B 90/36; A61B 34/10; A61B 90/96;
(Continued)

(56) References Cited

U.S. PATENT DOCUMENTS

| 5,610,811 A | 3/1997 | Honda |
| 6,701,174 B1 | 3/2004 | Krause et al. |

(Continued)

FOREIGN PATENT DOCUMENTS

| EP | 2618313 B1 | 7/2014 |
| WO | WO-2005084570 A1 | 9/2005 |

(Continued)

OTHER PUBLICATIONS

U.S. Appl. No. 15/919,139, filed Mar. 12, 2018, Augmented Reality Diagnosis Guidance.

(Continued)

*Primary Examiner* — Serkan Akar
*Assistant Examiner* — Renee C Langhals
(74) *Attorney, Agent, or Firm* — Schwegman Lundberg & Woessner, P.A.

(57) ABSTRACT

A system and method for tracking an object within a surgical field are described. A system may include a mesh of cameras distributed around the surgical field, the mesh of cameras including, for example at least three cameras. Cameras in the mesh of cameras may be in known positions or orientations relative to the surgical field or may be mobile with position or orientation to be determined by the system. The system may include a computing system communicatively coupled to the mesh of cameras, the computing system including a processor and a memory device. The computing system may be used to generate tracking data for a tracked object from images or image data taken by one or more cameras of the mesh of cameras.

18 Claims, 16 Drawing Sheets

(51) Int. Cl.

| | | |
|---|---|---|
| *G02B 27/01* | (2006.01) | |
| *A61B 34/10* | (2016.01) | |
| *A61B 90/00* | (2016.01) | |
| *H04N 13/156* | (2018.01) | |
| *H04N 13/344* | (2018.01) | |
| *H04N 13/366* | (2018.01) | |
| *A61B 34/00* | (2016.01) | |
| *H04N 5/232* | (2006.01) | |
| *G01S 5/16* | (2006.01) | |
| *G06T 7/292* | (2017.01) | |
| *H04N 5/33* | (2006.01) | |
| *H04N 13/239* | (2018.01) | |
| *A61B 90/96* | (2016.01) | |
| *A61B 90/50* | (2016.01) | |
| *H04N 13/00* | (2018.01) | |

(52) U.S. Cl.
CPC ............... *G01S 5/16* (2013.01); *G01S 5/163* (2013.01); *G02B 27/0172* (2013.01); *G06T 7/292* (2017.01); *G06T 19/006* (2013.01); *H04N 5/232* (2013.01); *H04N 5/23299* (2018.08); *H04N 5/33* (2013.01); *H04N 13/156* (2018.05); *H04N 13/239* (2018.05); *H04N 13/344* (2018.05); *H04N 13/366* (2018.05); *A61B 90/96* (2016.02); *A61B 2034/107* (2016.02); *A61B 2034/2048* (2016.02); *A61B 2034/2055* (2016.02); *A61B 2034/2065* (2016.02); *A61B 2034/252* (2016.02); *A61B 2090/0818* (2016.02); *A61B 2090/365* (2016.02); *A61B 2090/372* (2016.02); *A61B 2090/3983* (2016.02); *A61B 2090/502* (2016.02); *G06T 2207/10016* (2013.01); *H04N 2013/0081* (2013.01)

(58) Field of Classification Search
CPC ...... A61B 2090/502; A61B 2034/2048; A61B 2090/365; A61B 2034/2065; A61B 2034/2055; A61B 2034/252; A61B 2090/0818; A61B 2090/372; A61B 2090/3983; A61B 2034/107; H04N 5/23299; H04N 5/232; H04N 5/33; H04N 13/239; H04N 13/156; H04N 13/344; H04N 13/366; H04N 2013/0081; G01S 5/163; G01S 5/16; G06T 7/292; G06T 19/006; G06T 2207/10016; G02B 27/0172; G02B 2027/0198; G02B 2027/0141
USPC ......................................................... 600/424
See application file for complete search history.

(56) References Cited

U.S. PATENT DOCUMENTS

| | | |
|---|---|---|
| 7,383,073 B1 | 6/2008 | Abovitz et al. |
| 7,835,784 B2 | 11/2010 | Mire et al. |
| 8,100,133 B2 | 1/2012 | Mintz et al. |
| 8,233,963 B2 | 7/2012 | Hartmann et al. |
| 8,425,523 B2 | 4/2013 | Aram et al. |
| 8,600,478 B2 | 12/2013 | Verard et al. |
| 8,884,618 B2 | 11/2014 | Mahfouz |
| 9,105,207 B2 | 8/2015 | Leung |
| 9,248,000 B2 | 2/2016 | Sarvestani et al. |
| 9,492,240 B2 | 11/2016 | Itkowitz et al. |
| 9,538,962 B1 | 1/2017 | Hannaford et al. |
| 9,665,960 B1 | 5/2017 | Masters et al. |
| 9,718,190 B2 | 8/2017 | Larkin et al. |
| 9,757,087 B2 | 9/2017 | Simon et al. |
| 9,788,907 B1 | 10/2017 | Alvi et al. |
| 9,836,654 B1 | 12/2017 | Alvi et al. |
| 9,847,044 B1 | 12/2017 | Foster |
| 9,888,967 B2 | 2/2018 | Granchi et al. |
| 9,892,564 B1 | 2/2018 | Cvetko et al. |
| 9,898,664 B2 | 2/2018 | Matsuzaki |
| 9,918,740 B2 | 3/2018 | Uthgenannt et al. |
| 9,922,172 B1 | 3/2018 | Alvi et al. |
| 10,008,017 B2 | 6/2018 | Itkowitz et al. |
| 10,105,149 B2 | 10/2018 | Haider et al. |
| 10,169,696 B2 | 1/2019 | Lee |
| 10,235,807 B2 | 3/2019 | Thomas et al. |
| 10,575,905 B2 | 3/2020 | Nash et al. |
| 2002/0163499 A1 | 11/2002 | Sauer |
| 2003/0176783 A1 | 9/2003 | Hu |
| 2004/0044295 A1 | 3/2004 | Reinert et al. |
| 2004/0046711 A1 | 3/2004 | Triebfuerst |
| 2006/0043179 A1 | 3/2006 | Nycz et al. |
| 2006/0142657 A1 | 6/2006 | Quaid et al. |
| 2006/0142739 A1 | 6/2006 | Disilestro et al. |
| 2007/0136218 A1 | 6/2007 | Bauer |
| 2007/0249967 A1 | 10/2007 | Buly et al. |
| 2008/0200926 A1 | 8/2008 | Verard et al. |
| 2009/0017430 A1 | 1/2009 | Muller-daniels et al. |
| 2010/0159434 A1* | 6/2010 | Lampotang ............ G09B 23/30 434/365 |
| 2010/0311028 A1 | 12/2010 | Bell, III et al. |
| 2011/0093087 A1 | 4/2011 | Mcmahon et al. |
| 2012/0075343 A1 | 3/2012 | Chen et al. |
| 2013/0191099 A1 | 7/2013 | Krekel |
| 2013/0267838 A1 | 10/2013 | Fronk et al. |
| 2014/0081659 A1 | 3/2014 | Nawana et al. |
| 2014/0188240 A1 | 7/2014 | Lang et al. |
| 2014/0272866 A1 | 9/2014 | Kim |
| 2014/0275760 A1 | 9/2014 | Lee et al. |
| 2015/0297313 A1* | 10/2015 | Reiter ................. A61B 5/7267 600/408 |
| 2015/0366628 A1 | 12/2015 | Ingmanson |
| 2016/0035108 A1* | 2/2016 | Yu ........................ A61B 34/20 382/131 |
| 2016/0089153 A1 | 3/2016 | Couture et al. |
| 2016/0106554 A1 | 4/2016 | Lavallee |
| 2016/0154620 A1 | 6/2016 | Tsuda |
| 2016/0191887 A1 | 6/2016 | Casas |
| 2016/0225192 A1* | 8/2016 | Jones ...................... G06F 3/017 |
| 2016/0228193 A1 | 8/2016 | Moctezuma de la Barrera et al. |
| 2016/0249989 A1 | 9/2016 | Devam et al. |
| 2016/0287337 A1 | 10/2016 | Aram et al. |
| 2016/0324580 A1 | 11/2016 | Esterberg |
| 2017/0027651 A1 | 2/2017 | Esterberg |
| 2017/0169561 A1 | 6/2017 | Mullins |
| 2017/0202630 A1 | 7/2017 | Gerstner |
| 2017/0255450 A1 | 9/2017 | Mullins et al. |
| 2017/0258526 A1 | 9/2017 | Lang |
| 2017/0292827 A1* | 10/2017 | Haverkamp ............ G01B 11/26 |
| 2017/0312031 A1 | 11/2017 | Amanatullah et al. |
| 2017/0312032 A1 | 11/2017 | Amanatullah et al. |
| 2017/0337402 A1 | 11/2017 | Todeschini |
| 2017/0360513 A1 | 12/2017 | Amiot et al. |
| 2018/0021097 A1 | 1/2018 | Quaid et al. |
| 2018/0032130 A1 | 2/2018 | Meglan |
| 2018/0071032 A1 | 3/2018 | De Almeida Barreto |
| 2018/0082480 A1 | 3/2018 | White et al. |
| 2018/0090029 A1 | 3/2018 | Fisher et al. |
| 2018/0098813 A1 | 4/2018 | Nesichi et al. |
| 2018/0116823 A1 | 5/2018 | Johannaber et al. |
| 2018/0256256 A1 | 9/2018 | May et al. |
| 2018/0256258 A1 | 9/2018 | Nash et al. |
| 2018/0279913 A1* | 10/2018 | Frasier .................. A61B 6/545 |
| 2018/0338814 A1 | 11/2018 | Saget et al. |
| 2021/0030479 A1* | 2/2021 | Marti ..................... A61B 34/20 |

FOREIGN PATENT DOCUMENTS

| | | | |
|---|---|---|---|
| WO | 2015192117 | 12/2015 | |
| WO | WO-2016133644 A1 | 8/2016 | |
| WO | WO-2017115227 A1 * | 7/2017 | ............ A61B 34/32 |
| WO | WO-2018052966 A1 | 3/2018 | |

(56) References Cited

FOREIGN PATENT DOCUMENTS

| WO | WO-2018169891 A1 | 9/2018 |
|---|---|---|
| WO | WO-2018052966 A8 | 10/2018 |

OTHER PUBLICATIONS

U.S. Appl. No. 15/703,239, filed Sep. 13, 2017, Augmented Reality Surgical Technique Guidance.
"U.S. Appl. No. 15/703,239, Non Final Office Action dated Jun. 19, 2019", 33 pgs.
"U.S. Appl. No. 15/703,239, Response Filed Sep. 19, 2019 to Non-Final Office Action dated Jun. 19, 2019", 13 pgs.
"International Application Serial No. PCT US2018 022074, International Preliminary Report on Patentability dated Sep. 26, 2019", 12 pgs.
"U.S. Appl. No. 15/919,139, Notice of Allowance dated Oct. 16, 2019", 9 pgs.
"U.S. Appl. No. 15/703,239, Advisory Action dated Jan. 30, 2019", 4 pgs.
"U.S. Appl. No. 15/703,239, Response filed Feb. 8, 2019 to Final Office Action dated Nov. 8, 2018", 13 pgs.
"U.S. Appl. No. 15/919,139, Response filed Apr. 12, 2019 to Final Office Action dated Feb. 12, 2019", 13 pgs.
"U.S. Appl. No. 15/919,139, Advisory Action dated May 13, 2019", 3 pgs.
"U.S. Appl. No. 15/919,139, Final Office Action dated Feb. 12, 2019", 16 pgs.
"U.S. Appl. No. 15/919,139, Examiner Interview Summary dated Apr. 12, 2019", 3 pgs.
"International Application Serial No. PCT US2017 051312, International Preliminary Report on Patentability dated Mar. 28, 2019", 15 pgs.
"U.S. Appl. No. 15/703,239, Response Filed Aug. 31, 2018 to Non-Final Office Action dated Jun. 1, 2018", 11 pgs.
"U.S. Appl. No. 15/703,239, Non Final Office Action dated Jun. 1, 2018", 17 pgs.
"International Application Serial No. PCT/US2017/051312, International Search Report dated Feb. 5, 2018", 7 pgs.
"International Application Serial No. PCT/US2017/051312, Invitation to Pay Additional Fees and Partial Search Report dated Dec. 8, 2017", 15 pgs.
"International Application Serial No. PCT/US2017/051312, Written Opinion dated Feb. 5, 2018", 13 pgs.
"International Application Serial No. PCT/US2018/022074, International Search Report dated Jun. 6, 2018", 8 pgs.
"International Application Serial No. PCT/US2018/022074, Written Opinion dated Jun. 6, 2018", 10 pgs.

Stefl, M., et al., "Spinopelvic mobility and acetabular component position for total hip arthroplasty", Bone Joint J 2017, (2017), 9 pgs.
"U.S. Appl. No. 15/703,239, Final Office Action dated Nov. 8, 2018", 24 pgs.
"U.S. Appl. No. 15/703,239, Response filed Jan. 8, 2019 to Final Office Action dated Nov. 8, 2018", 11 pgs.
"U.S. Appl. No. 15/919,139, Non Final Office Action dated Oct. 10, 2018", 15 pgs.
"U.S. Appl. No. 15/919,139, Response Filed Jan. 10, 2019 to Non-Final Office Action", 9 pgs.
Delp, Scott L, et al., "Surgical Simulation: An Emerging Technology for Training in Emergency Medicine", Presence: Teleoperators and Virtual Environments 6:2; 147-159, (1997), 14 pgs.
"U.S. Appl. No. 15/703,239, Final Office Action dated Dec. 11, 2019", 31 pages.
"U.S. Appl. No. 15/703,239, Examiner Interview Summary dated Mar. 9, 2020", 3 pages.
"U.S. Appl. No. 15/703,239, Response filed Mar. 11, 2020 to Final Office Action dated Dec. 11, 2019", 15 pages.
"Australian Application Serial No. 2018236172, First Examination Report dated Jun. 3, 2020", 4 pages.
"European Application Serial No. 18717148.3, Response to Communication pursuant to Rules 161(1) and 162 EPC filed Jun. 2, 2020", 27 pages.
"U.S. Appl. No. 15/703,239, Non Final Office Action dated Aug. 24, 2020", 27 pages.
"Software-Guided Knee Surgery-Balance in Motion", Brainlab, [Online] Retrieved from the Internet: URL: https: www.youtube.com watch?v=m8YPSSpPsiw, (Jul. 19, 2017), 03:32 min; 56 pages.
"Augmented Reality Is Changing Neurosurgery For the Better", Futurism, [Online] Retrieved from the Internet: URL: https: www.youtube.com watch?v=7xZBS5K65EA, (Oct. 25, 2016), 00:46 min.; 9 pages.
"European Application Serial No. 17778014.5, Communication pursuant to Rule 164(2)(b) and Article 94(3) EPC dated Sep. 7, 2020", 11 pages.
"U.S. Appl. No. 15/703,239, Response filed Dec. 28, 2020 to Non Final Office Action dated Aug. 24, 2020", 14 pages.
"Canadian Application Serial No. 3,055,941, Office Action dated Dec. 3, 2020", 6 pages.
"U.S. Appl. No. 15/703,239, Final Office Action dated Mar. 30, 2021", 35 pgs.
"Australian Application Serial No. 2018236172, Response filed Jan. 18, 2021 to First Examination Report dated Jun. 3, 2020", 17 pgs.
"Canadian Application Serial No. 3,055,941, Response filed Apr. 6, 2021 to Office Action dated Dec. 3, 2020", 21 pgs.
"U.S. Appl. No. 15/703,239, Appeal Brief filed Aug. 2, 2021", 17 pgs.

\* cited by examiner

SURGICAL FIELD CAMERA SYSTEM THAT ONLY USES IMAGES FROM CAMERAS WITH AN UNOBSTRUCTED SIGHT LINE FOR TRACKING

CLAIM OF PRIORITY

This application claims the benefit of U.S. Provisional Patent Application Ser. No. 62/540,207, filed on Aug. 2, 2017 and claims the benefit of U.S. Provisional Patent Application Ser. No. 62/616,264, filed on Jan. 11, 2018, the benefit of priority of each of which is claimed hereby, and each of which are incorporated by reference herein in its entirety.

BACKGROUND

Cameras, object recognition technology, and tracking systems may be utilized to assist with surgical operations. This technology may be used to locate surgical instruments or track the location of patient operational points. Previous systems relied on a single camera or viewpoint. In the surgical field, object recognition and object tracking with a single camera or viewpoint proves difficult as the surgeons may block the camera. Additionally, because of the confined working space and the size of the instruments, portions of the tracked objects may be occluded. This type of occlusion may cause the single camera tracking or object recognition to lose the object. Thus, while present navigation devices are generally well accepted and provide useful capabilities, there exists room for improving the reliability and usability of tracking technology in surgery.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
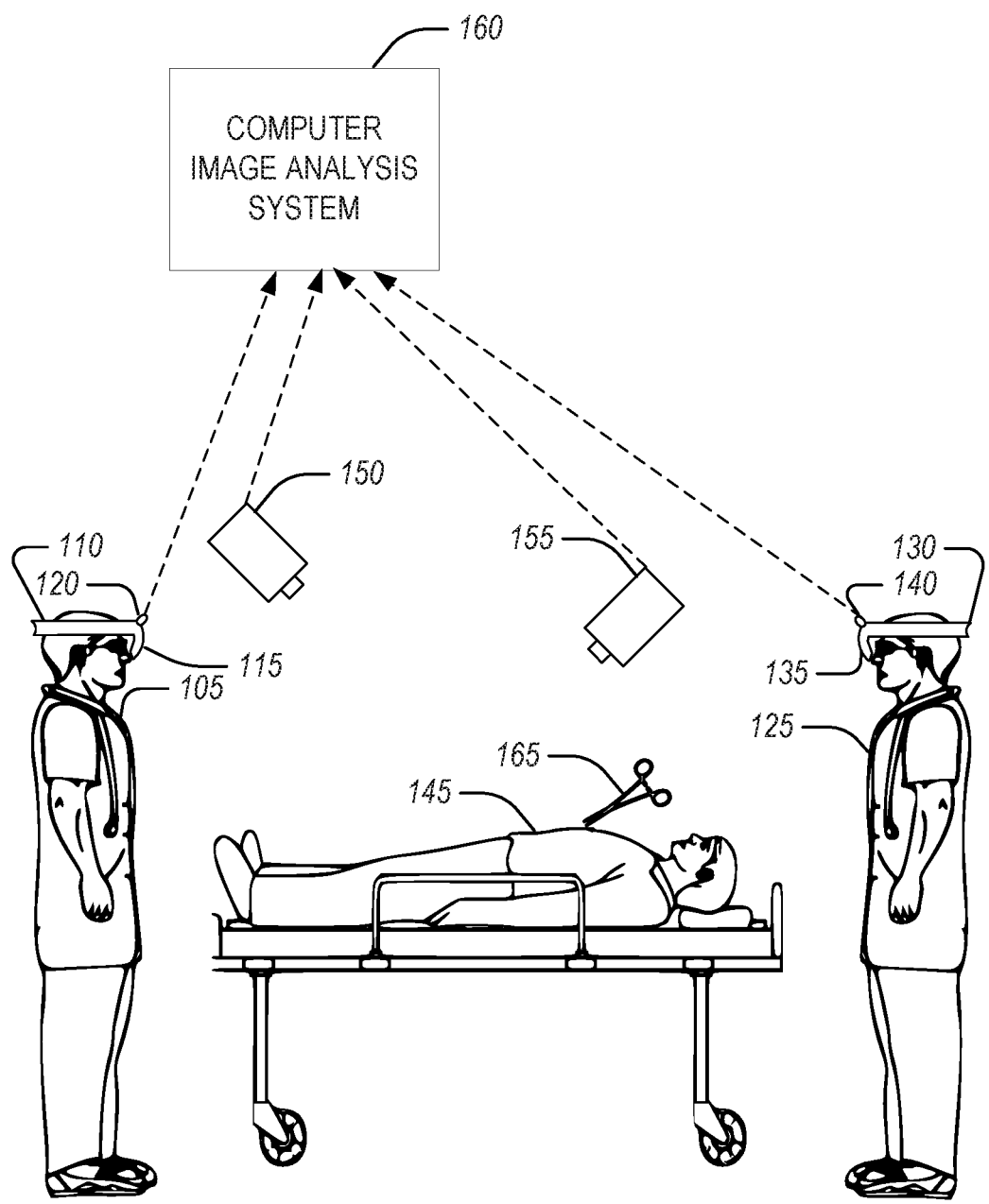
FIG. 1 illustrates a surgical field camera system in accordance with some embodiments.

Systems and methods for using an augmented reality device during a surgical procedure are described herein. The systems and methods herein describe uses for the augmented reality device, such as to display virtual components or representations of real objects overlaid on a real environment. An augmented reality (AR) device allows a user to view displayed virtual objects that appear to be projected into the real environment, which is also visible. AR devices typically include two display lenses or screens, including one for each eye of a user. Light is permitted to pass through the two display lenses such that aspects of the real environment are visible while also projecting light to make virtual elements visible to the user of the AR device.

In an example, some traditional surgical navigation and robotics systems utilize single-point stereo infrared cameras and reflective trackers to identify landmarks or instruments and provide tracking during surgery. These systems are limited by line-of-sight that can be disrupted frequently during a surgical procedure. In this specification, "track" refers to the process of continually determining the position and orientation of any object or optical tracker in a three-dimensional space, for example the three-dimensional space of the surgical field.

In an example, digital video cameras may be used for object recognition and positional tracking. The positional data and tracking accuracy may be insufficient for facilitating the precision needed in surgical applications. Augmented reality or mixed reality headsets may be used to assist in surgery. Head-worn cameras on these devices offer a close proximity view to the operative field, but may be subject to line-of-sight problems.

By utilizing multiple cameras, or a camera mesh, surgical navigation or robotics systems may properly track a surgical instrument, body part, or surgical landmark and eliminate problems that arise from a single camera described above. An optical tracker may also be attached to an object in an optical tracking system. The optical tracking system, as an example, may utilize multiple cameras, or a camera mesh, to track an object by tracking the position and orientation of the optical tracker. The camera mesh may comprise different types of cameras positioned in various places around a surgical field. Examples of cameras that may be incorporated into a camera mesh and their placement include an overhead stationary camera, an overhead tracking camera, glasses with an attached camera, an AR headset with attached camera, a camera attached to a surgical instrument, or a body camera. The camera mesh may include a camera device, where a camera device may include a single camera, a single housing with two cameras, such as for taking stereoscopic images and video recordings, a plurality of cameras, or the like. Stereoscopic images may be used to determine depth. The examples of cameras may include an infrared camera, a depth camera, or an infrared detection device, such as the Kinect from Microsoft of Redmond, Wash.

During a surgical operation, time and precision are critical. In many cases, the surgeon is responsible for directing the whole surgical procedure. This can be difficult as the surgeon is responsible for performing the surgery, but also directing other members of the surgical team and properly handling any unexpected occurrences. Utilizing multiple highly trained surgeons or surgical assistants may alleviate these issues, but may also create problems when time is critical and decisions have to be made. A surgical field camera system may assist members of the surgical team, during both normal and emergency operating procedures by helping guide and identify the best tools and steps to complete the procedures.

A surgical field camera system may comprise a camera mesh of multiple cameras communicatively coupled to a computer image analysis system. By utilizing the camera mesh and the computer image analysis system, objects involved in the surgical procedure may be tracked, such as instruments (e.g., scalpel, implant insertion tools), a body part, or an implant. A single camera system may suffer tracking issues as line-of-sight disruptions may cause the system to lose the tracking on an object. Additionally, the movements of the surgical team may be limited by the use of a traditional tracking system, as the surgical team members will seek to prevent occlusions caused by their motions. Line-of-sight disruptions are common in the surgical realm as objects or tools may be inserted into the body of the patient and thus become sufficiently occluded to prevent a single camera from tracking the object or tool. A camera mesh system with a computer image analysis system, capable of recognizing a three-dimensional object, may track an object or tool throughout the surgical operation. Tracking an object is not limited to a tool or instrument used by the surgeon. The tracked object may include a body part, such as a leg or hand, the location of an incision, the positioning of a bone inside the body part, or the location of an organ within the patient. The surgical field camera system may track multiple objects simultaneously. The surgical field camera system may analyze the captured images received from each camera in a camera mesh to determine the camera with the best captured image of the cameras in the camera mesh. The best captured image of captured images received from the camera mesh may be determined by factors such as the least obstructed view of the tracked object, the clearest captured image, the captured image with the highest resolution, and the captured image with the highest contrast.

FIG. 1 illustrates a surgical field camera system 100 in accordance with some embodiments. In FIG. 1, two members of the surgical team are shown, including a first surgeon 105 and a second surgeon 125. A first AR headset 110 is worn by the first surgeon 105 and a second AR headset 130 is worn by the second surgeon 125. Each AR headset 110, 130, may have a display portion 115, 135, and a camera 120, 140. Each AR headset 110, 130 may also include inertial sensors (e.g., gyroscope, accelerometer, magnetometer) for tracking the position and orientation of the AR headset. The surgical field may have camera devices in a fixed position, such as first camera device 150 and second camera device 155. First camera device 150 and second camera device 155 may be moveable camera devices, such as a camera device attached to a track along the ceiling to allow the camera device to be moved to different locations within the surgical field. A camera device may be stationed on a motorized cart that may be moved to different locations within the surgical field. The first camera device 150 and second camera device 155 may be mechanized with the ability to rotate and adjust the angulation up and down. In a mechanized camera example, the first camera device 150 and second camera device 155 may be attached to robotic positioning device with known position and orientation relative to the surgical field, which allows for the camera angles and viewpoint to be carefully tracked. In the example embodiment, the surgical field system 100 includes a camera mesh comprising a first AR headset camera 120, a second AR headset camera 140, a first camera device 150, and a second camera device 155.

In an example, each camera including first AR headset camera 120, second AR headset camera 140, first camera device 150, and second camera device 155, is communicatively coupled to the computer image analysis system 160. Each camera device transmits synchronized captured images to the computer image analysis system 160. The computer image analysis system analyzes the captured images for a tracked object. In the example system 100, a tracked object 165 may be an instrument used by the surgeons, such as forceps. The first camera device 150 and the second camera device 155 may use infrared light to detect the tracked object 165 in a field of view. The computer image analysis system 160 may evaluate the detection (e.g., captured images) of the camera devices to identify portions of the tracked object 165.

During the surgical operation, first surgeon 105 may bend over to perform operations on patient 145 and the view of the tracked object 165 for first camera device 150 may become obstructed. The computer image analysis system 160 may then analyze the captured images from all communicatively coupled cameras to determine other camera devices with the corresponding captured images with the least occlusion of the tracked object 165, such that the surgical field camera system 100 may continue tracking the tracked object 165 without interruption. In the example scenario, the computer image analysis system 160 may analyze the captured images from first AR headset camera 120, second AR headset camera 140, first camera device 150, and second camera device 155. The computer image analysis system 160 may determine the captured image from first camera device 150 does not include the tracked object 165 as first surgeon 105 has occluded the view. The computer image analysis system 160 analyzes the captured images and determines second AR headset camera 140 does not include tracked object 165 as its field of view is not directed to the operating area of patient 145. The computer image analysis system 160 may then determine portions of the tracked object 165 are present in captured images from the first AR headset camera 120 and the second camera device 155. The computer image analysis system continues tracking the tracked object 165 using the captured images from first AR headset camera 120 and the second camera device 155. In an examples utilizing images from an AR headset camera, the AR headsets can be tracked within the surgical field through other cameras in the tracking system (such as first camera device 150 and second camera device 155) or through sensors internal to the AR headsets. In some examples, precise tracking of position and orientation of the AR headsets is needed to translate position and orientation information within images capture by the AR headsets into useful tracking data within the virtual 3D surgical field.

Figure 2:
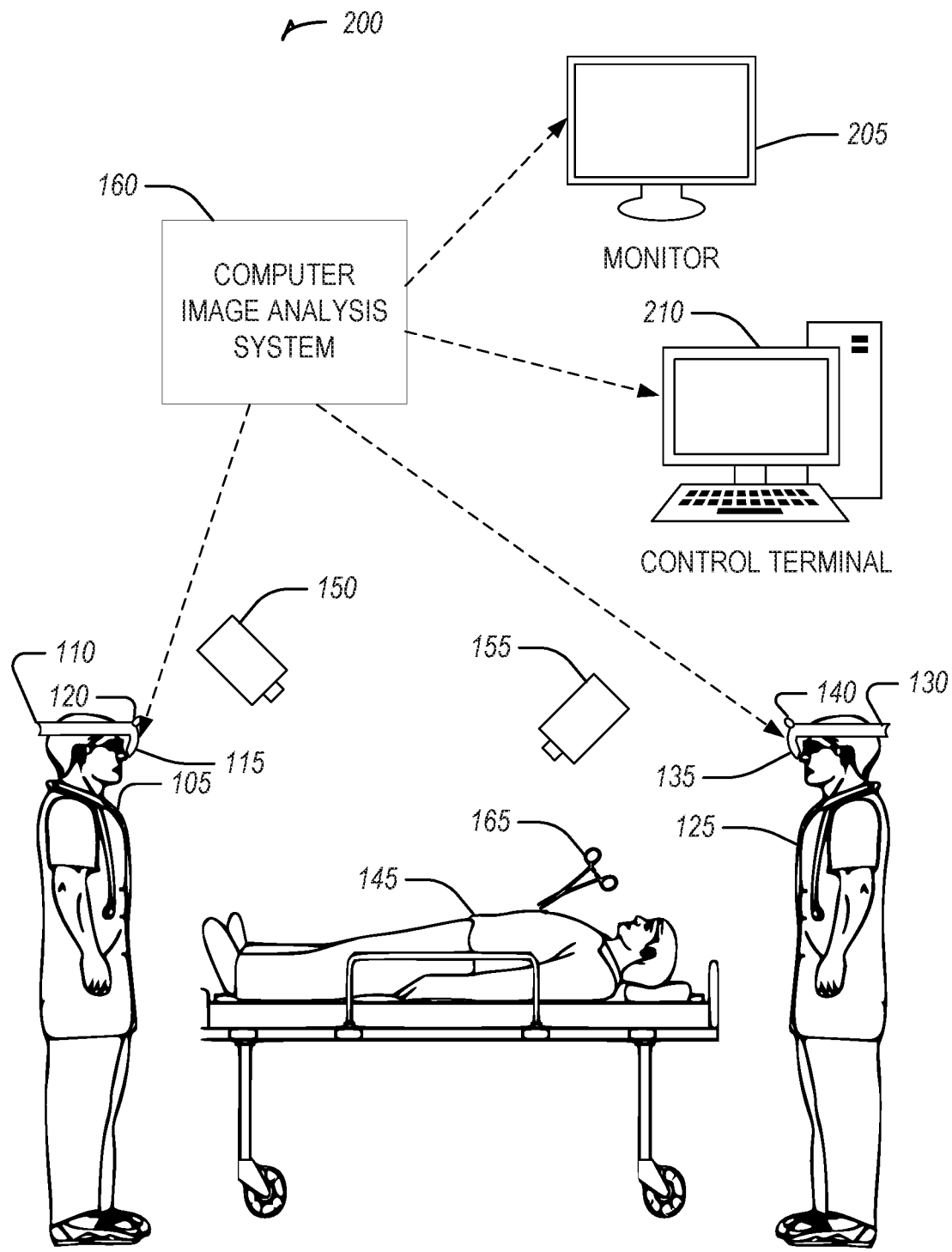
FIG. 2 illustrates a surgical field camera system in accordance with some embodiments.

FIG. 2 illustrates a surgical field camera system 200 in accordance with some embodiments. In an example, the system 200 includes a device for viewing and controlling the tracking of objects, such as monitor 205 or control terminal 210. To facilitate the tracking of an object, such as tracked object 165, the computer image analysis system 160 receives captured images from multiple cameras in the camera mesh, such as first AR headset camera 120, second AR headset camera 140, first camera device 150, or second camera device 155. The computer image analysis system 160 analyzes the captured images to determine the captured image and corresponding camera devices with the best line-of-sight to continue tracking an object. Based on the captured images and the determined best line-of-sight, the computer image analysis system 160 may generate different outputs for each type of communicatively coupled display device.

In an example, a monitor 205 may be communicatively coupled to the computer image analysis system 160. The monitor 205 may receive and display a video feed of the determined best line-of-sight camera for the tracked object 165. The monitor 205 may be placed in the surgical field for the surgical team to view as the operation proceeds. The monitor may be outside the surgical field to allow others, such as students, to observe the operation. As the computer image analysis system 160 analyzes the captured images received from the camera mesh and determines the best line-of-sight for the tracked object 165, the video output to the monitor 205 is updated in real time. In another example, the monitor 205 may receive the captured image feeds from the camera mesh, or some combination of captured image feeds. The determined best line-of-sight camera for the tracked object 165 may be indicated among the images displayed at the monitor. The display may include a composite image generated from multiple sources. For example, the composite image may be generated to create a simulated image of the surgical field from preferred or predetermined viewing angle. The simulated image may be generated such that the viewing angle is displayed regardless of a camera device capturing that viewing angle.

In an example similar to the monitor 205, a control terminal 210 may be communicatively coupled to the computer image analysis system 160. The control terminal 210 may receive and display a video feed of the determined best line-of-sight camera device for the tracked object 165. The control terminal 210 may receive the captured image feeds from the camera mesh, or some combination of captured image feeds. The control terminal 210 may include controls for a user at the terminal to interact with the system. For example, a user at the control terminal 210 may control which objects are tracked by the system. At stages of the operation, different objects may be tracked, wherein the user may control which object to track at each stage. The user at the control terminal 210 may have control over the positioning of some camera devices in the camera mesh. The control terminal 210 user may determine one of the camera devices no longer has any line-of-sight to the object, and change the positioning and direction of the camera device through user interface controls at the control terminal 210. The control terminal 210 user may provide information to a surgeon using an AR headset. Through the user interface of the control terminal 210, the user may type a message to the surgeon, such as surgeon 105, so that the message is received by AR headset 110 and shown on the AR display 115 for surgeon 105. Thus surgeon 105 may receive information during the operation without diverting the surgeon's attention away from the operation.

The selection of an object to track or the tracked object display output (if the camera mesh allows for multiple objects to be tracked simultaneously) may be automated. The steps of the surgical procedure may be programmed into the computer image analysis system 160. Based on the programming the analysis system may track an object corresponding to the current step of the procedure, wherein the computer image analysis system 160 automatically determines the object to track for the step and analyzes the captured images to locate and begin tracking the object.

The computer image analysis system 160 may transmit data to a communicatively coupled AR headset display as an example. In the system 200, first AR headset 110 and second AR headset 130 may receive data transmissions from the computer image analysis system 160 to augment the view seen by first surgeon 105 and second surgeon 125, respectively. As an example, the computer image analysis system 160 may be configured to send data to each AR headset about the location of the tracked object 165. This may include data such as arrows that appear on the AR headset display to direct the surgeon to the location of the tracked object 165 when the tracked object is not within the view or line-of-sight of the surgeon. Additionally, the sent data may include highlighting or other indicators to bring attention to the tracked object when it is within the view or line-of-sight of the surgeon.

By utilizing the AR displays, such as first AR display 115 and second AR display 135, the computer image analysis system 160 may combine the tracked object data with the images received from a respective AR headset. The information presented to each surgeon with their respective AR headsets may be relevant to their personal line-of-sight. Displaying information in perspective to second camera device 155 for either the first surgeon 105 or second surgeon 125 may be confusing for a surgeon. Instead, as an example, the computer image analysis system 160 may utilize the recognition and positional data of the tracked object 165 and correlate the data to the captured images received from first AR camera 120 and second AR camera 140. Continuing the example, first camera device 150 and second camera device 155, based on the known location of the camera devices, may have the best ability to track the tracked object 165 and thus be used for recognition and positional data. The computer image analysis system 160 may then determine if the tracked object is included within the captured images received from first AR camera 120 and second AR camera 140. As an example, the tracked object may be within the line-of-sight of first AR camera 120 (and thus within the view of first surgeon 105) but may not be within the line-of-sight of second AR camera 140 (and thus not within the view of second surgeon 125). The computer image analysis system 160 may utilize the captured images from first AR camera 120 to determine the visible aspects of tracked object 165 and transmit information to first AR headset 110 such that the first AR headset display 115 highlights the visible portions of the tracked object 165 for first surgeon 105. The computer image analysis system 160 may utilize the captured images from second AR camera 140 to determine the position of tracked object 165 in reference to the direction of second AR headset 130 and transmit information to second AR headset 130 such that the second AR headset display 135 displays an indication of the location of the tracked object 165 for second surgeon 125.

Multiple sources of captured image data may be used to provide greater positional accuracy. For example, in order to provide accuracy in positional tracking, two or more camera devices may be used at a minimum distance of separation (e.g., IR Optical Navigation). In an example, the system 200, first camera device 150 and second camera device 155 may be fixed at a minimum distance of separation to provide positional tracking information. The surgical field camera system 200 may utilize a camera mesh of multiple camera devices to triangulate the position of an object in space and track its location. The more camera devices in the camera mesh ensure that as line-of-sight is interrupted from one camera device, other camera devices may be substituted to generate positional calculations. A user, such as the user of the control terminal 210, may be given an indication of current system accuracy based on how many camera device sources are currently being utilized. This accuracy information may be displayed at the control terminal 210 as an accuracy strength indicator. For certain steps of a surgical procedure, the user may elect not to improve line of sight, instead waiting on the improvement for the most critical steps of a procedure. In some examples, each camera device, such as the first camera device 150, may include multiple cameras mounted a fixed distance from each other providing triangulation capabilities within each camera device.

In an example, the surgical field camera system 200 includes a camera mesh of at least three camera devices for multiple source tracking of an object. The surgical field camera system 200 uses multiple sources of captured images (e.g., multiple camera devices from the camera mesh) to track a single object. No one single source is a primary source for tracking the object. By utilizing multiple sources for the tracking of an object, the surgical field camera system may construct a virtual three-dimensional representation of the object based on a set of multiple viewpoints provided by the multiple sources. The surgical field camera system may utilize information provided by other sources, such as three-dimensional Computer Aided Design (CAD) models of instruments, three-dimensional images of the patient, and measurements of the patient's anatomy (e.g., height, weight, leg length). In certain examples, this additional information can be used to enhance the system's ability to reconstruct virtual representations of the objects within the surgical field. The virtual three-dimensional representation of the object may be utilized for displaying the virtual object. For example, the virtual three-dimensional representation may be utilized in the display of an AR headset (e.g., 110 or 130) to fill in the portions of the tracked object that are occluded from the AR headset wearer's view. The surgical field camera system 200 may monitor the strength of tracking accuracy for each of the sources. For example, an accuracy threshold may be set such that when the accuracy strength of a source drops below the threshold, the surgical field camera system may stop utilizing the source for tracking the object. In another example, when the accuracy strength of a source drops below the threshold, the surgical field camera system may reposition the camera until the accuracy strength exceeds the threshold.

The surgical field camera system 200 may be configured in many ways for tracking an object or an optical tracker. An example embodiment may utilize two camera devices, where the two camera devices each have two cameras. The camera devices may use infrared light to track an object or an optical tracker. In this example, the camera devices may be located at fixed positions within a surgical field. When a line of sight is obstructed for a first camera of a first camera device of the camera device setup or for the first camera device entirely, a second camera device of the two camera device setup may be used to continue tracking the position of the tracked object or optical tracker. When only one of the cameras (e.g., the first camera) of the first camera device is blocked, the second camera device may be used with or without additional image information from a remaining cameras of the first camera device. In an example, the two camera device setup may be extended to include three or more camera devices. The three or more camera devices may be organized in the surgical field to have different line of sights to a tracked object or optical tracker, such that when a line of sight for one or more cameras or camera devices become obstructed, remaining camera devices may be used to continue seamlessly tracking the object or the optical tracker. In an example, the camera devices may include stereoscopic cameras (e.g., two cameras within a single housing), and when a line of sight of one of the two cameras within the single housing is obstructed, information from the other camera of the two cameras may be discarded.

In another embodiment, the surgical field camera system may utilize three or more camera devices, each with a single camera (e.g., the camera devices may not be stereoscopic). The three camera embodiment may allow for one of the cameras to be blocked and still track an object or an optical tracker. For example, the computer image analysis system 160 may receive image data from the three or more camera devices and determine a location of the tracked object or the optical tracker from the image data. The computer image analysis system 160 may be configured to be able to track objects or optical trackers using data from any two or more cameras of the three or more camera devices. When a line of sight to the object or the optical tracker becomes obstructed for one of the three or more cameras, data from the remaining two or more cameras may be used to continue to reliably track the object or the optical tracker. In an example, using more than three camera devices may allow for redundancy, particularly when the camera devices are located in close proximity and may potentially have blocked sight lines simultaneously.

In an example, a combination of camera devices, including a camera device having a single camera and a camera device having two or more cameras may be used to track an object or an optical tracker. For example, the object or optical tracker may be consistently tracked when some sight lines are blocked, when at least two cameras have clear sight lines. For example, one camera device may be sufficient when the camera device has two or more cameras, two camera devices may be sufficient when the two camera devices each have a single camera, two camera devices may be sufficient when one of the two camera devices has a single camera and the other has two cameras, with one or fewer of its cameras obstructed, or any other combination of two or more cameras (e.g., including additional redundant cameras).

In an example, a camera device may be attached to a motorized stand. The motorized stand may be moved around the surgical field, either manually or by remote. A camera device on a motorized stand may be attached to a track for consistent movement and known positioning.

In an example, surgical field camera system 200 may include a camera located on an AR headset or a camera worn on a person, such as a camera attached to a headband or a pair of glasses. Location data for the position of the camera devices, such as that provided by inertial sensors, may allow for the head worn camera to be utilized as a tracking camera device.

In an example, the surgical field camera system 200 may switch between camera devices for tracking an object as the view from a camera device becomes obstructed or other factors prevent proper tracking by a camera device in the surgical field. Any number of camera devices, such as two or more camera devices may be utilized at any given time in parallel for tracking an object. When the view of a camera device becomes obstructed, the surgical field camera system may recalibrate the other camera devices with unobstructed views based on receiving tracking data from one less camera device.

The surgical field camera system may extrapolate the positioning and orientation of the tracked object as less camera devices are available with a view to the tracked object while the system determines if any camera devices are available for tracking the object. For example, the surgical field camera system may be tracking an object with an attached optical tracker. The surgical field camera system, for the sake of processing, may only utilize camera devices that can detect three or more reflective components of the optical tracker, as the primary camera devices. Should the view of multiple primary camera devices become obstructed, the surgical field camera system may utilize camera devices in the camera mesh which are detecting less than three reflective components (but at least one) of the optical tracker. Based on the detected reflective components and the position and orientation information provided by the remaining primary camera devices, the surgical field camera system may extrapolate the position of undetected reflective components and thus the position and orientation of the optical tracker.

The surgical field camera system 200 may use a threshold for a minimum number of reflective components that are to be detected for tracking of the optical tracker to continue. The threshold may include a collective minimum, for example, across all camera devices in the camera mesh, or a minimum per camera device. For example, when at least five reflective components are detected at a camera device or in the camera mesh then tracking may continue. There may also be a minimum number of camera devices, which are each relied on to detect a minimum number of reflective components. For example, when at least three camera devices are detecting three or more reflective components, then tracking may continue uninterrupted. If the number detected components is nearing the threshold minimum in these examples, then an alert may triggered or an automatic repositioning of one or more camera devices may occur. The surgical field camera system 200 may have a secondary threshold for extrapolating the position of the reflective components. For example, a minimum primary threshold may be at least three camera devices detecting at least three reflective components each for continuous normal tracking. In another example, a secondary minimum threshold of at least three cameras detecting at least two reflective components each for interpolated tracking may be used.

AR is a technology for displaying virtual or "augmented" objects or visual effects overlaid on a real environment. The real environment may include a room or specific area, or may be more general to include the world at large. The virtual aspects overlaid on the real environment may be represented as anchored or in a set position relative to one or more aspects of the real environment. For example, a virtual object may be configured to appear to be resting on a table. An AR system may present virtual aspects that are fixed to a real object without regard to a perspective of a viewer or viewers of the AR system. For example, a virtual object may exist in a room, visible to a viewer of the AR system within the room and not visible to a viewer of the AR system outside the room. The virtual object in the room may be displayed to the viewer outside the room when the viewer enters the room. In this example, the room may act as a real object that the virtual object is fixed to in the AR system.

An AR system may be viewable to one or more viewers, and may include differences among views available for the one or more viewers while retaining some aspects as universal among the views. For example, a heads-up display may change between two views while virtual objects may be fixed to a real object or area in both views. Aspects such as a color of an object, lighting, or other changes may be made among the views without changing a fixed position of at least one virtual object.

A user may see a virtual object presented in an AR system as opaque or as including some level of transparency. In an example, the user may interact with the virtual object, such as by moving the virtual object from a first position to a second position. For example, the user may move an object with his or her hand. This may be done in the AR system virtually by determining that the hand has moved into a position coincident or adjacent to the virtual object (e.g., using one or more cameras, which may be mounted on an AR device or separate, and which may be static or may be controlled to move), and causing the virtual object to move in response. Virtual aspects may include virtual representations of real world objects or may include visual effects, such as lighting effects, etc. The AR system may include rules to govern the behavior of virtual objects, such as subjecting a virtual object to gravity or friction, or may include other predefined rules that defy real world physical constraints (e.g., floating objects, perpetual motion, etc.). An AR device may include the camera. The camera may include an infrared camera, an infrared filter, a visible light filter, a plurality of cameras, a depth camera, etc. The AR device may project virtual items over a representation of a real environment, which may be viewed by a user.

The surgical field camera system 200, utilizing a camera mesh—including camera devices and cameras on AR headsets worn by one or more members of the surgical team, may track objects such as surgical instruments, external and internal body parts, and incisions. The system may track an object such that when a user of an AR headset views a tracked object, the view is augmented such that the tracked object is highlighted. For example, at a step in a surgery, a surgeon may need an instrument for inserting a bone implant. When the surgeon views a tray of instruments for the procedure, the bone implant insertion instrument may appear highlighted through the AR view. When the surgeon finishes placing the implant, the next step may be to screw the implant in place. When the surgeon next views the tray of instruments, the implant insertion instrument is no longer highlighted, and instead the screwdriver may be highlighted. The surgeon may view a set of screws, with the appropriate screws for the implant highlighted.

An orthopedic implant may be accompanied with a set of screws from the manufacturer. The set of screws includes several different subsets of screws for securing the implant in the body. Not all screws may be intended to be used, instead the doctor may select a subset of screws appropriate for the patient. To avoid any confusion, surgical field camera system 200, with the AR headset worn by the surgeon, may track the subset of screws necessary for the current procedure. The surgeon's view, through the AR headset, may then highlight the appropriate subset of screws so the surgeon has no difficulty differentiating between the subsets of screws. This may speed up the procedure and reduce the chance of mistake. In another example, a second doctor may be monitoring the surgical procedure and the tracked set of screws at a terminal monitor. As the surgical procedure progresses, the second doctor may perform an analysis of the patient's bones (and thus allowing the surgeon to concentrate on the surgery) to determine the appropriate subset of screws to use for the implant. The second doctor may then select a subset of screws which may then be highlighted for the surgeon in the surgeon's AR headset.

The surgical field camera system 200 comprises a mesh of camera devices distributed around the surgical field. The camera devices may be stationary or mobile. The camera mesh may include multiple camera devices. Each camera device in the camera mesh may be at a known position and orientation relative to the surgical field. Some cameras may be mobile, such as a camera as part of an AR headset. The position of the AR headset user may be recorded before the surgery begins, or the headset may include a location and inertial sensors to report the positioning of the user and thus the camera.

A computer image analysis system 160 may be communicatively coupled to the camera mesh. The computer image analysis system 160 includes a processor and a memory device, such as a personal computer or server. The memory device includes software instructions for executing the image analysis and object tracking.

The computer image analysis system 160 may receive synchronized image captures from multiple camera devices in the camera mesh. Each image may be designated with an identification of the camera device which captured it. The identification of the camera device, and the camera or cameras within the camera device, for each image or for received image data may be used to correlate data about the camera device, such as location and positioning, to the image or image data. At least a portion of the synchronized image captures includes information indicative of a position and orientation of a tracked object within the surgical field. For example, the camera mesh may include two overhead camera devices (e.g., 150 and 155) and a camera (e.g., 120 or 140) on the AR headset (e.g., 110 or 130) worn by the surgeon (e.g., 105 or 125). One of the overhead camera devices and the AR headset camera may capture an instrument being used by the surgeon, but the second overhead camera device may not capture the instrument as the surgeon is blocking the line-of-sight.

The computer image analysis system may analyze the synchronized image captures. The analysis may include object recognition, wherein the system attempts to identify objects in the images based on a library of objects known to the system. The system may be instructed to find specified objects in the images. For example, a user may program the system with the instruments which may be used for a surgical operation. The system may then focus the image analysis on detecting only the instruments that are in use and not searching for instruments that are not present in the surgical field. The object may include a part of a patient's anatomy. For example, a user may program the system with information about the patient's body part, such as the left leg, that will be operated on during the surgical operation. The system may use information about the location and direction of each camera. The tracking data for an identified object may be generated from information extracted from at least two of the synchronized images.

The tracking data may then be used to determine a position and an orientation of the tracked object within a virtual three-dimensional coordinate system. The tracking data may include the position and direction of the camera devices. The tracking data may include the previous images and tracking data of the tracked object. For example, the system may be tracking an object with a camera mesh comprising camera devices A, B, and C. The object may be tracked based on images received from camera devices A and B. Should the line-of-sight for camera device A be disrupted, the system may keep tracking the object with camera devices B and C, based on, in part, the previous tracking data received from camera device A which may help indicate the location the object may be at.

The system may output the position and the orientation of the tracked object. The output data may be actual data such as coordinates in a virtual three-dimensional coordinate system. The output may be one or more of the captured synchronized images that includes the tracked object. The output images may be augmented, for example, the tracked object may be highlighted with a color, arrows or other lines may point to the tracked object, or the image may contain data about the positioning and orientation of the object. If the object is an instrument with settings, such as a screwdriver with variable torque, the current torque setting may be included in the output. The output may be sent to an AR headset communicatively coupled to the system. The output may contain data for augmenting the view of the wearer of the AR headset. For example, this may include data to highlight the tracked object. The augmentation may include supplemental information about the object, such as the previously noted torque setting, or instructions for the next step of the procedure based on the position and orientation of the tracked object. The user of the AR headset may turn and change their view, such that the tracked object is no longer within the line-of-sight of the AR headset user, the augmented view may display arrows to indicate where the tracked object is located. The AR headset user may not lose valuable time looking for instruments as the system may point the user towards the instrument they need.

The analysis of the synchronized images by the system may include determining a tracking strength indicator for each captured synchronized image. The tracking strength may be based on a value for the object recognition indicating how strong the recognition analysis may be. The tracking strength indicator may be based on determining how much of an aspect of the tracked object is occluded in each image of the synchronized image captures. The tracking strength indicator may be based on the previous captured images from each camera, such as the number of previous images captured from a camera device including the tracked object. The system may utilize each captured synchronized image that includes a tracking strength indicator which exceeds a predetermined threshold. The predetermined threshold may be set by a user or determined over time through machine learning. The predetermined threshold value may be implemented to remove false positive tracking identifications from a camera device.

In an embodiment, the surgical field camera system 200 may include an instrument controller. The instrument controller may receive the position and the orientation of the tracked object, with the tracked object being an instrument. The instrument may be a surgical tool for which electronic control is necessary, such as a drill or screw driver. The instrument controller may then analyze the position and orientation to determine if the instrument is in the proper position and orientation for performing the operation. This may include determining if the instrument is within a specified range for the operation. If the instrument controller determines the position and orientation is within the required range for the operation, then power is supplied to the instrument or other control mechanisms are released so the instrument may function.

In an embodiment, the surgical field camera system 200 may include a surgical robot. The surgical field camera system 200 utilizes object recognition and positional data from multiple sources, such as the camera mesh, and analyzes the data to provide accurate, uninterrupted information for the navigation of robotics equipment in the surgical field. Robotics have become a useful tool for assisting the surgeon in the surgical field. A robotic device may assist in the surgical field performing tasks such as biopsies, electrode implantation for functional procedures (e.g., stimulation of the cerebral cortex, deep brain stimulation), open skull surgical procedures, endoscopic interventions, other "keyhole" procedures, arthroplasty procedures, such as total or partial knee replacement, hip replacement, shoulder implant procedures, or the like. The surgical field camera system 200 with a communicatively connected robotic device may transmit position and the orientation of a tracked object to the robotic device. The surgical field camera system 200 may track the robotic device to ensure it is performing operations at the correct position and orientation. Confirming the position and orientation of the tracked object, the robotic device, or both, a surgical tool portion of the robotic device may be actuated.

The camera mesh of the surgical field camera system 200 may be configured, in an embodiment, to add one or more additional camera devices to the mesh of cameras. The surgical field camera system 200 including the computer image analysis system may receive synchronized image captures from the additional camera device in combination with the captured images received from the camera devices previously in the camera mesh. The surgical field camera system 200 may calibrate the additional camera device including calibration steps to determine the position and the orientation of the additional camera relative to a virtual three-dimensional coordinate system that encompasses a working portion of the surgical field. The calibration of the additional camera device may cause the surgical field camera system 200 to measure the position and the orientation of the additional camera device relative to at least one other camera device in the camera mesh.

The surgical field camera system 200 may include a camera or camera device on an AR headset in the camera mesh for tracking an object. A location of the AR headset and camera may be determined, for example by the computer image analysis system 160 to determine the location of the tracked object. For example, the AR camera may be moved (e.g., by a person wearing the AR camera). While the AR camera may retain a line of sight to the tracked object, the location or orientation of the tracked object may not be determinable when AR camera moves. The surgical field camera system 200 may not be able to determine whether the AR camera moved alone and the tracked object did not move, or whether the AR camera and the tracked object moved. In order to determine the location and orientation of the tracked object using the AR camera, a location and orientation of the AR camera may be determined.

Determining the location and orientation of the AR camera may be performed in a number of ways. In an example, the location and orientation of the AR camera may be determined using one or more sensors located on the AR headset. For example, an accelerometer, gyroscope, magnetometer, GPS, local positioning system sensor (e.g., using NFC, RFID, beacons, Wi-Fi, or Bluetooth within a surgical field), or the like may be used. In another example, the AR headset may determine its position and orientation using the AR camera and information from the surgical field, such as predetermined markers, locations, stickers, walls, corners of a room, or the like. In yet another example, the location and orientation of the AR headset may be determined using another camera device within the surgical field, such as a camera dedicated to following the AR headset or any camera that has a line of sight to the AR headset (e.g., from among the cameras in the camera mesh).

In an example, the location and orientation of the AR headset may be determined on the AR headset, for example using a processor of the AR headset, and for example without using a computer image analysis system 160 separate from the AR headset (e.g., the computer image analysis system 160 may run on the AR headset). In this example, the AR headset may determine its location using one or more of the examples listed above. The AR headset may determine respective locations and orientations of other cameras in the camera mesh. After determining the locations and orientations of the AR headset and any other cameras in the camera mesh, image data from the AR camera and the other cameras in the camera mesh may be used to determine the location or orientation of the tracked object. When a line of sight to the tracked object is blocked for the AR camera or one of the other cameras in the camera mesh, the AR headset may automatically determine the best camera(s) to continue tracking the tracked object based on previous image data. In an example, the AR headset may include a preferred camera device to track the object. The preferred camera device may include a depth camera, two cameras, or the like. The preferred camera device may be preferred due to its likely proximity to the tracked object, lower likelihood of a blocked line of sight, or surgeon preference. In another example, a camera of the AR headset may act as a backup camera, such as one to be used only when sight lines of one, more than one, or all of the other cameras of the camera mesh are obstructed or partially obstructed. In another example, the AR camera may be an ordinary member of a camera mesh.

In an embodiment, the surgical field camera system 200 may be utilized to monitor the number of an items used during a surgical procedure. In an example, sponges and gauze are utilized during a surgical procedure to soak up blood and other liquids such that the surgeon has a clean operating area. Multiple sponges or gauze may be utilized, wherein the sponge or gauze may be inserted into the patient to keep the area of surgery clean. One potential risk of the use of sponges or gauze during surgical operations is the risk of leaving a sponge or gauze in the patient. By utilizing the surgical field camera system 200 to monitor the number or location of sponges or gauze used, incidents of materials left in patients may be prevented. For example, the surgical field camera system 200 may track a sponge used during the surgery. The system may track the sponge as it is inserted into the patient. The system may then increase a sponge counter once the sponge has been full inserted into the patient. The system may then decrease the count when it tracks a sponge being removed from the patient. The system may display, such as on a monitor or an AR headset display, the total sponge count such that a member of the surgical team may confirm the count for the number of inserted sponges is zero before completing the surgery. In an example, the system may track or recognize when the operating area of the patient is being sutured and produce an alarm if the sponge count is not at zero.

Figure 3:
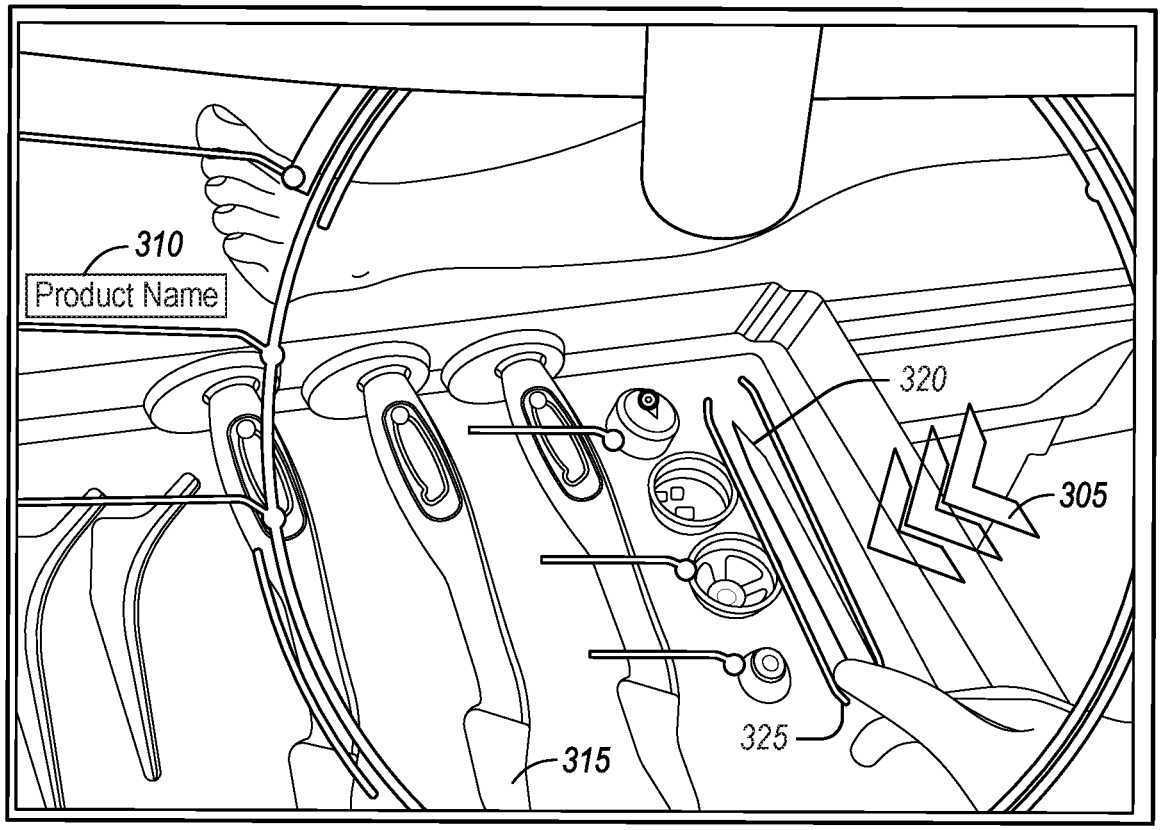
FIG. 3 illustrates an augmented reality (AR) viewpoint when locating an instrument, in accordance with some embodiments.

FIG. 3 illustrates an AR viewpoint when locating an instrument, in accordance with some embodiments. In an example, an augmented view 300 includes the AR viewpoint, for example, as seen by a surgeon wearing an AR headset. The AR viewpoint is augmented to include information overlaid onto what the surgeon may be looking at to help guide the surgeon through a procedure. In the example augmented view 300, a scalpel 320 may be the tracked object. The scalpel 320 is highlighted with brackets 325 and arrows 305 to indicate the location. The augmented view 300 may include additional information 310 for the surgeon such as product name and condition. The system may be tracking other objects, such as instrument 315 such that when the surgeon requires the instrument, the system may locate it.

Figure 4:
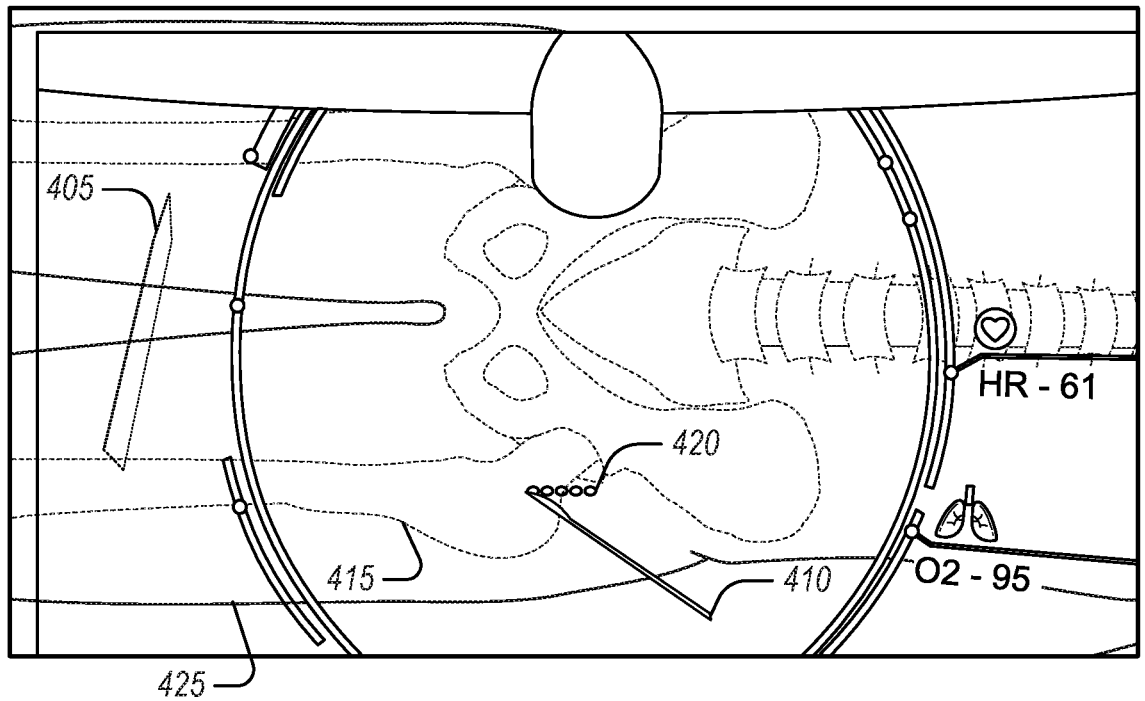
FIG. 4 illustrates an AR viewpoint indicating a location to make an incision, in accordance with some embodiments

FIG. 4 illustrates an AR viewpoint indicating the location to make an incision, in accordance with some embodiments. In an example, an augmented view 400 includes the AR viewpoint as seen by a surgeon wearing an AR headset. In an example, the augmented view 400 includes augments to the surgeon's view, such as an indicator 405 for a current instrument 410 being used. The surgical field camera system may track instruments such as instrument 410 and may track a body or a body part such as a patient leg 425. Based on the tracked position of patient leg 425 or utilizing additional information gathered from sources such as x-rays and computerized tomography (CT) scans, the surgical field camera system may determine the positioning of the patient's bones. The augmented view 400 for the surgeon may then display the positioning of the patient's bones 415 to help guide the surgeon during an operation, even though the surgeon cannot actually see the bones. In addition, the surgical field camera system may transmit information to the surgeon's AR headset for guiding the surgeon during the operation, such as the correct location for an incision 420.

The use of an AR headset or mixed reality headset for surgical instrument navigation may be useful in multiple orthopedic surgery applications. An example of use for the surgical field camera system may be to provide tracking and visualization for surgical instruments when they may be otherwise occluded or not visible to the surgical team. For example, an instrument or instrument and implant combination may be tracked and a virtual model of the physical object may be presented to a surgeon in a mixed reality setting allowing the surgeon to visualize the instrument or implant in space even when it is not physically visible to them. An example situation occurs when a surgeon inserts a femoral stem or trauma rod into the bone. The occluded part of the instrument and implant may be overlaid in a mixed reality view allowing the surgeon to visualize the trajectory or the fit of the device. This functionality may be further enhanced by the use of multiple camera devices. In another example, a stem inserter or broach handle may be recognized and tracked by the camera device, and the surgeon may benefit from the mixed reality presentation of the data. If the object or instrument being tracked is occluded from the view of the surgeon's head worn camera, the system may utilize a camera worn by another member of the operative team, or a camera device placed remotely to identify and track the object or instrument. Sensors on the surgeon's head worn device may be used to establish the surgeon's relationship to the object being tracked. The system may adjust the data being presented to the surgeon in such a way as to recognize the surgeon's point of view in the surgical field while using the measurement data from another member of the operative team. In this way, each user of the system may benefit from the line-of-sight of other users or camera devices mounted in the surgical field.

Figure 5:
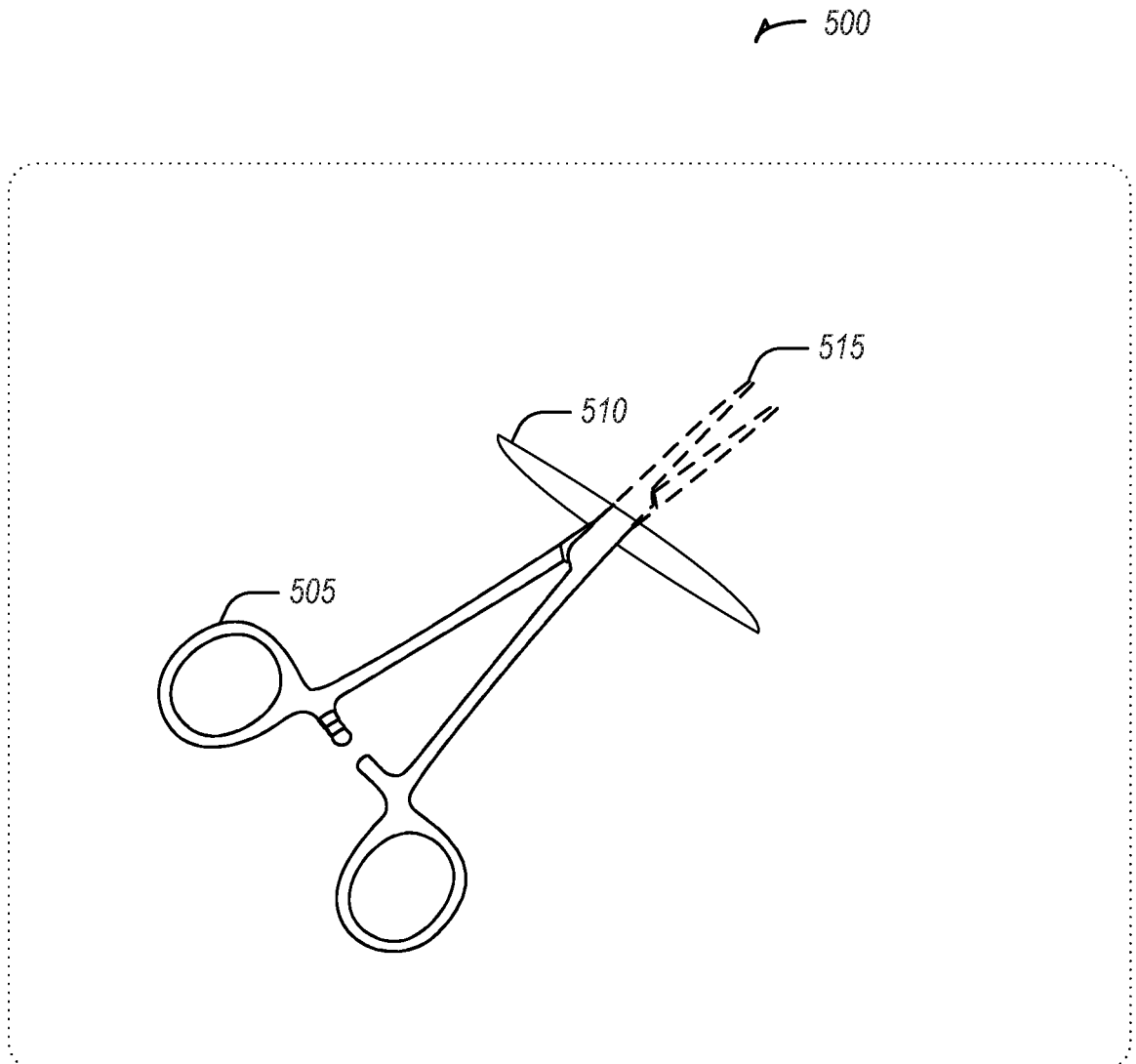
FIG. 5 illustrates an AR viewpoint when a portion of a tracked object is occluded, in accordance with some embodiments.

FIG. 5 illustrates an AR viewpoint when a portion of a tracked object is occluded, in accordance with some embodiments. In an example, an augmented view 500 includes the AR viewpoint, for example, as seen by a surgeon wearing an AR headset. In an example, the augmented view 500 includes a pair of forceps 505 as the tracked object. The surgeon may be able to see the forceps 505 before the operation, but once the surgeon inserts the forceps 505 into an incision 510, a portion of the forceps 505 is occluded and the surgeon may no longer be able to see the positioning of the functional end of the forceps 505. As the forceps 505 may be a tracked object in the surgical field camera system, the system may determine, based on the visible portion of the forceps 505, the positioning and functional state (e.g., for the example forceps, whether the forceps are in an open or closed state) of the occluded portion. The system may then transmit information to the surgeon's AR headset to augment the surgeon's view such that the surgeon may view a generated image of the occluded portion of the forceps 515. The system may continue to track position and orientation of the tracked object such that as the tracked object moves, the system transmits information to the surgeon's AR headset for the generated image of the tracked object to follow the movement of the tracked object. Utilizing multiple sources for captured images (e.g., the multiple cameras comprising the camera mesh), the system may determine the position and orientation of a tracked object. The multiple sources may provide functional information for the tracked object as well, such as in the example of the forceps 515, the system may determine if the forceps 515 are in an open or closed functional state. The multiple sources may provide multiple perspectives such that the system may determine the position and orientation of the tracked object in a three-dimensional space and generate a virtual three-dimensional representation of the tracked object.

Figure 6:
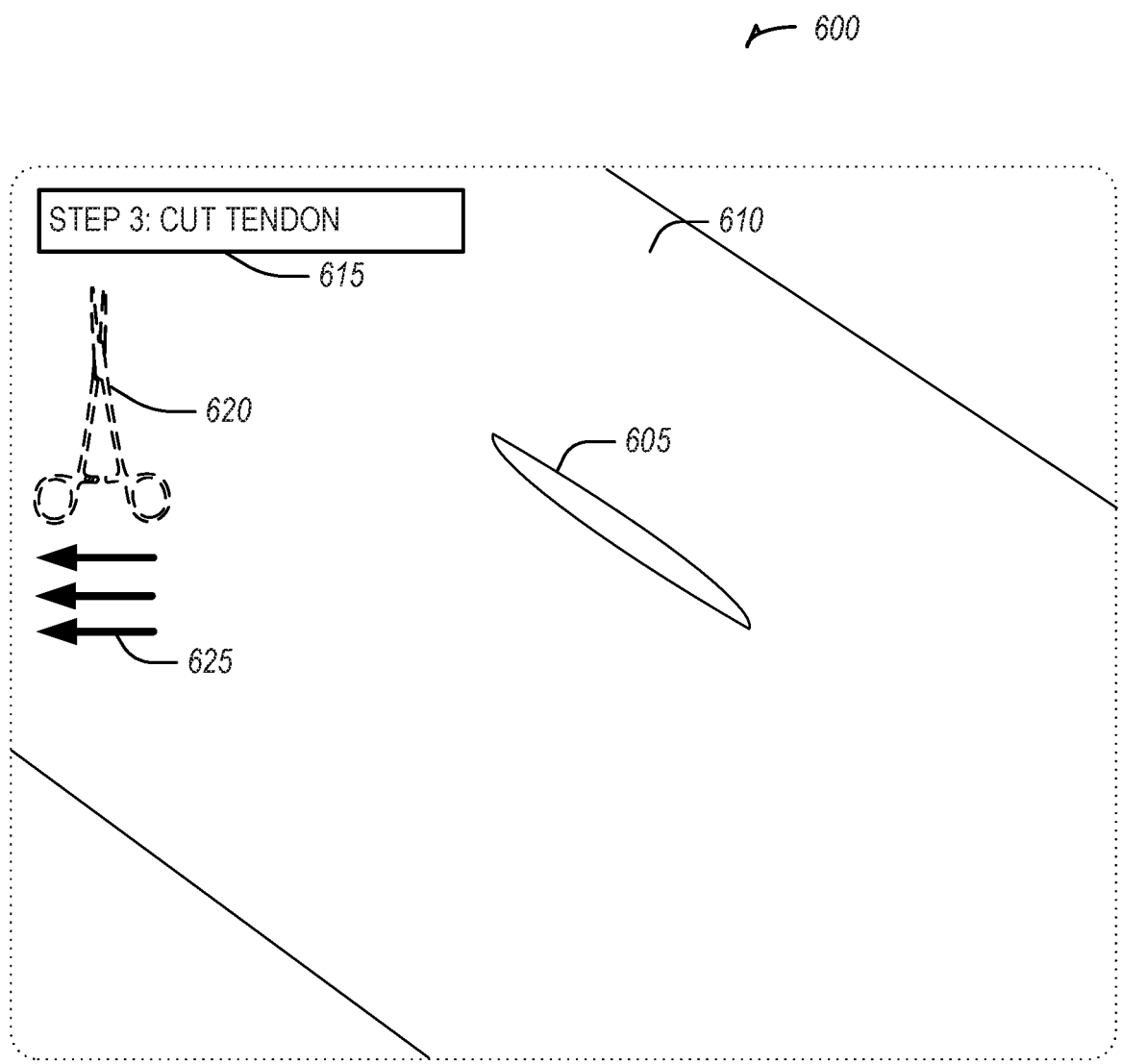
FIG. 6 illustrates an AR viewpoint with direction indicators to a tracked object, in accordance with some embodiments.

FIG. 6 illustrates an AR viewpoint with direction indicators to a tracked object, in accordance with some embodiments. In an example, an augmented view 600 includes the AR viewpoint, for example, as seen by a surgeon wearing an AR headset. In an example, the augmented view 600 includes an incision 605 on a body part 610 of a patient. In an example, instructions 615 may be presented on the AR display of the AR headset for a stage of a surgical operation. Additionally, the AR display may provide a virtual image of a surgical instrument 620 used for the stage of the surgical operation. In the example illustration, the surgical instrument 620 is a pair of forceps. The surgical field camera system may track the surgical instrument needed for each stage of the surgical operation. When the tracked surgical instrument is within the view of the surgeon, the computer image analysis system may transmit information to the AR headset worn by the surgeon such that the tracked surgical instrument is highlighted for the surgeon. In the example illustration of the augmented view 600, the tracked surgical instrument (i.e., the forceps) is not within the view of the surgeon. The computer image analysis system may determine the tracked surgical instrument is not within the view of the surgeon and then determine the location of the tracked surgical instrument relative to the surgeon's view. The computer image analysis system may analyze the captured images transmitted from a camera on the AR headset and determine, in comparison to the captured images from other sources in the surgical field camera system, the orientation of AR headset and surgeon. The computer image analysis system may receive orientation information for the AR headset based on sensors connected to the AR headset. The computer image analysis system may compare the location of the tracked object and the orientation of the AR headset to determine the positioning of the tracked object relative to the view of the surgeon wearing the AR headset. The computer image analysis system may then transmit information to the AR headset worn by the surgeon such that the AR display may display arrows 625 indicating the direction to the location of the tracked surgical instrument.

Figure 7:
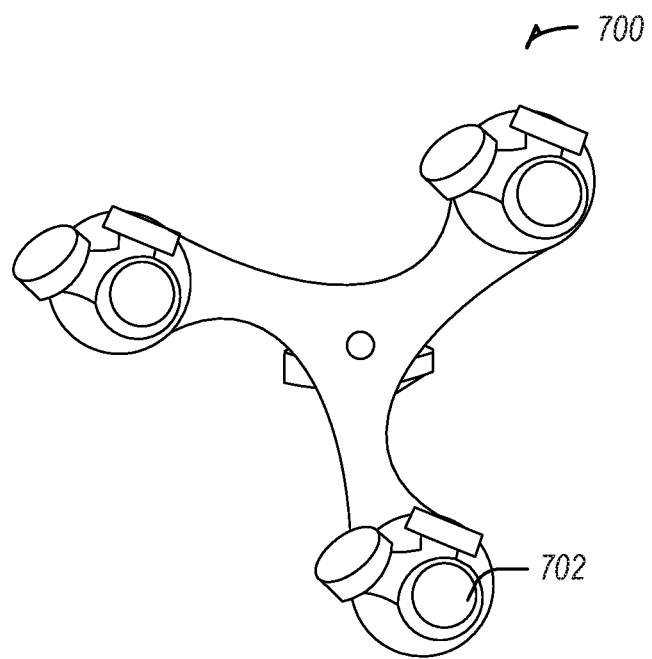
FIG. 7 illustrates an example of an optical tracker that may be attached to an object for tracking the object in an optical tracking system, in accordance with some embodiments.

FIG. 7 illustrates an example of an optical tracker 700 that may be attached to an object for tracking the object in an optical tracking system, in accordance with some embodiments. The optical tracker includes multiple reflective components (e.g., 702), each at a set position on the optical tracker (e.g., relative to one another). The optical tracker may be attached to an object in the surgical field such as an instrument or a body part. The position and orientation of the object relative to the object tracker is set and recorded such that the optical tracking system may know the position and orientation of the object by determining the position and orientation of the optical tracker. The position and orientation of the optical tracker may be determined by detecting the multiple reflective components (e.g., 702) and correlating the detected reflective sphere positioning to the known position of the multiple reflective components on the optical tracker 700.

Analysis of the synchronized images by the optical tracking system may include using a tracking frame for the tracked object. The optical tracker 700 is designated with a plurality of tracking markers such as at identifying points of the optical tracker. Once an optical tracker is recognized by the system, the system may assign tracking markers to the identifying points of the object. This may allow the system to track the object with less processing by identifying the tracking markers in each captured image instead of recognizing the entire object in each captured image. The system may use the tracking markers to determine how much of the aspect of the tracked object is occluded. By calculating the number of tracking markers visible in each of the synchronized captured images, the system may quickly and with less processing determine the amount of the tracked object that is occluded.

In an example embodiment, the surgical field camera system may include a camera mesh which includes at least camera devices. Each camera device may include a pair of infrared cameras to be a part of a same camera housing as an infrared camera device and placed in fixed positions within the surgical field. For example, the camera device may be an optical tracking system device, such as the Polaris from Northern Digital Inc. (NDI). The tracked object may have a plurality of infrared-reflective marker components attached to it, with the infrared-reflective marker components arranged rigidly in a specified orientation to one another. The plurality of infrared-reflective marker components may be attachable as a rigid structure to a surgical instrument or an anatomy of a patient. In the surgical field camera system, the computer image analysis system may be configured to generate tracking data using synchronized image captures from at least two cameras of the at least two camera devices.

Figure 8:
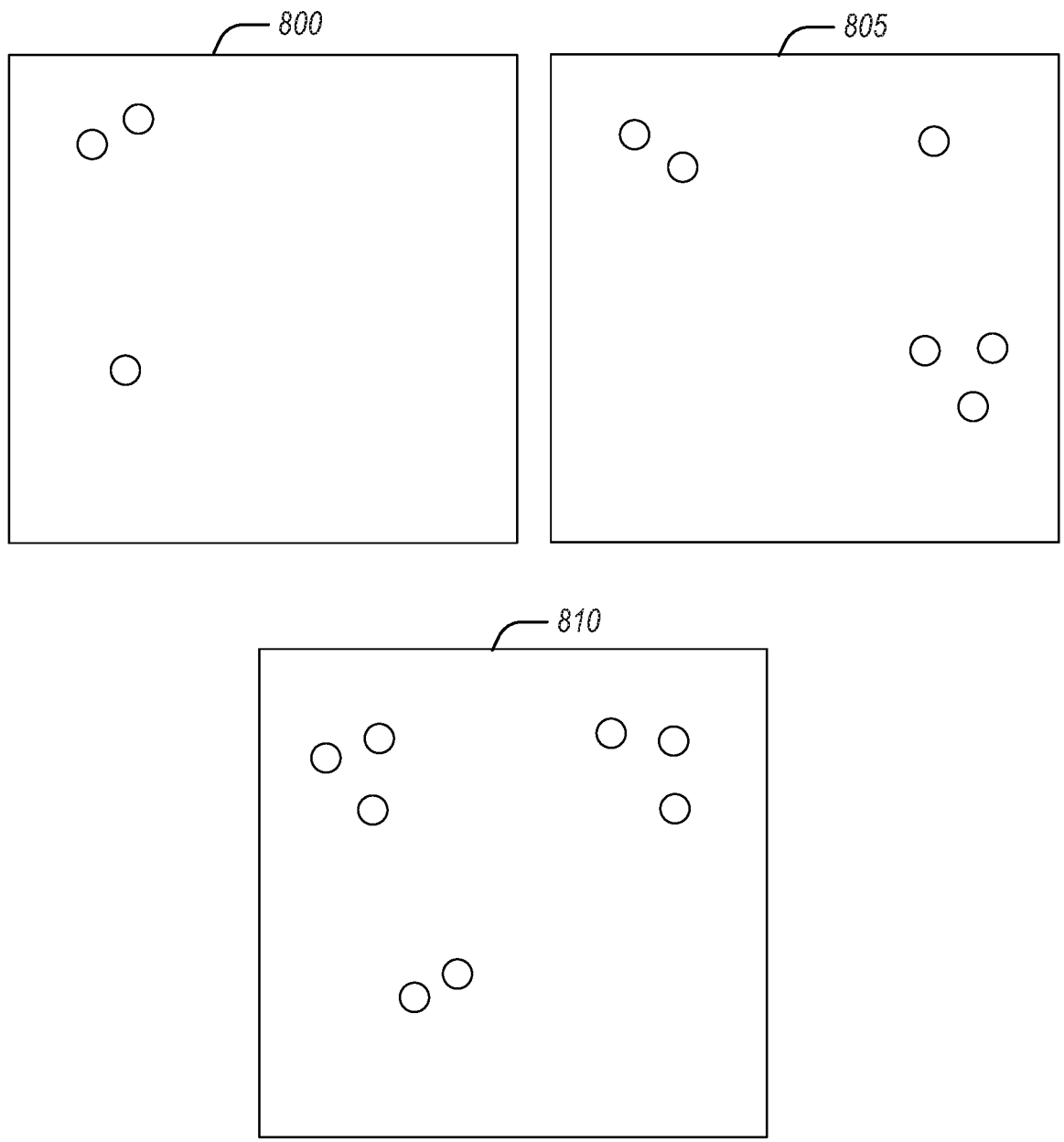
FIG. 8 illustrates an example of three images taken from three cameras in an optical tracking system, in accordance with some embodiments.

FIG. 8 illustrates an example of three images 800, 805, 810 taken from three cameras in an optical tracking system, in accordance with some embodiments. Each image 800, 805, 810 illustrates a different perspective of the how reflective components on the optical tracker may be seen by a computer image analysis system, in an embodiment. For each image 800, 805, 810, a number of the reflective components may be visible to a camera used to capture the images 800, 805, and 810. For example three reflective components are visible in image 800 (e.g., captured reflective component 801), six reflective components visible in image 805 (e.g., captured reflective component 806), and eight reflective components visible in image 810 (e.g., captured reflective component 811). The example images 800, 805, 810 may be stereoscopic images captured by one or more camera devices. The stereoscopic images may contain depth information and may allow for a position determination of the optical tracker to be made, such as by a computer image analysis system. The position or orientation information of an optical tracker may be determined using a single stereoscopic image. The computer image analysis system may determine the position and orientation of an optical tracker based on a number and position of the reflective components. In an example, the computer image analysis system may utilize factors such as the size, shape, and brightness of the reflective components. The optical tracker may have reflective components of varying size, shape, or reflectivity. The order and positioning of the varying size, shape, and reflectivity of the reflective components may be recorded in the computer image analysis system. The computer image analysis system may then use the known order and positioning of the reflective components to determine the position and orientation of the optical tracker dependent upon the size, shape, and reflectivity (e.g., the brightness) of the reflective components captured in an image.

In an example, a camera device that captured the image 810 may be selected as having a best line of sight to the optical tracker, for example based on the number of visible reflective components. The computer image analysis system may analyze the positioning of the reflective components in image 810 to determine the position and orientation of the optical tracker. In an example, a camera device that captured the image 800 may have a partially obstructed sight line to the optical tracker. Information from the camera device that captured the image 800 may be discarded or not used based on the partial obstruction. Information from a camera device that captured the image 805 may optionally be used to determine the position and orientation of the optical tracker. In a first example, the image 805 may be discarded and not used when the image 810 has sufficient information to determine the position and orientation of the optical tracker. In a second example, the image 805 may be used to check or verify that the position and orientation of the optical tracker was correctly determined from the information in the image 810. In a third example, both the image 805 and the image 810 may be used to determine the position and orientation of the optical tracker, for example by using a geometric average to determine locations of reflective components that are visible in both the image 805 and the image 810.

In an embodiment, depending on the number of visible components in a given captured image, the computer image analysis system may use multiple images to determine the position and orientation of the optical tracker. For example, when the camera producing image 810 is obscured such that the reflective sphered are no longer visible, the computer image analysis system may determine that image 800 and image 805, individually, do not have enough reflective components visible, but utilizing both image 800 and image 805, the computer image analysis system may determine the position and orientation of the optical tracker. In an example, the computer image analysis system may utilize any number of camera devices or images of the reflective components to determine the position and orientation of the optical tracker.

Factors such as the computer image analysis system having information for the position of the camera devices may affect the selection and number of images utilized for determining the position and orientation of the optical tracker. In an example, a default camera may be selected. In an example, an AR device may control the selection or number of images used for determining the position and orientation of the optical tracker. Preference may be given to a camera or camera device on the AR device or to a camera or camera device not on the AR device.

In an example, parts of images (e.g., parts of image data) may be used from more than one camera. For example, considering image 800 and image 805, when the images are taken by a camera device such as a depth camera, the images may be from a similar sight line (e.g., the cameras in the camera device may be separated by only a few inches or feet, and may be pointed in generally the same direction). In that case, the cameras of the camera device may both be partially obstructed. For example, captured reflective component 801 and captured reflective component 806 may be two parts of an optical tracker, where captured reflective component 801 shows up in image 800 and captured reflective component 806 shows up in image 805, but neither image includes both captured reflective components. Based on, for example, previous information (e.g., images taken before the partial obstruction or a known layout or orientation of the optical tracker), a composite image or image data may be constructed including the captured reflective component 801 and the captured reflective component 806 to determine a position or orientation of the optical tracker including the corresponding reflective components.

Figure 9:
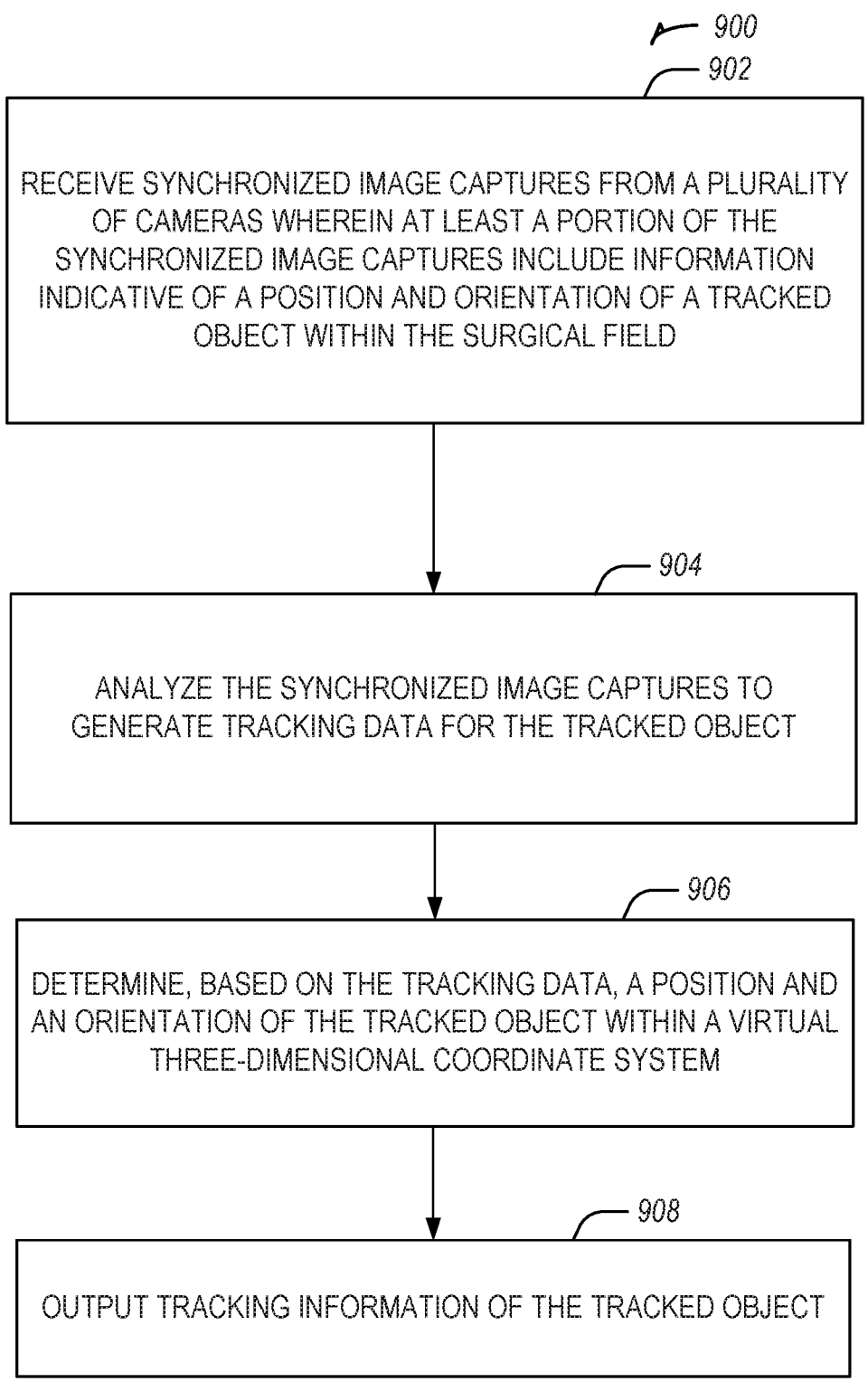
FIG. 9 illustrates a flow chart showing a technique for tracking an object using a camera mesh in the surgical field.

FIG. 9 illustrates a flow chart showing a technique 900 for tracking an object using a camera mesh in the surgical field. The technique 900 includes an operation 902 to receive synchronized image captures from a camera mesh wherein a portion of the images include information indicative to the position and orientation of a tracked object. The technique 900 includes an operation 904 to analyze the synchronized images to generate tracking data for the tracked object. The technique 900 includes an operation 906 to determine a position and orientation of the tracked object based on the tracking data. The technique 900 includes an operation 908 to output the position and orientation of the tracked object. The technique 900 may include further operations or elements, such as those described below in the various examples.

The technique 900 may include determining a tracking strength indicator for the synchronized captured images and utilizing the images which have a strength indicator that exceeds a predetermined threshold. The technique 900 may include determining the tracking strength by how much of an aspect of the tracked object is occluded in the synchronized captured images. The technique 900 may include using a tracking frame with tracking markers for the tracked object and determining the occluded aspect by the visibility of the tracking markers. The technique 900 may include using a surgical robot to receive a position and orientation for the tracked object and actuating a surgical tool with the surgical robot in response to the position and orientation of the tracked object. The technique 900 may include adding an additional camera to the camera mesh and receiving synchronized captured images from the additional camera.

Figure 10:
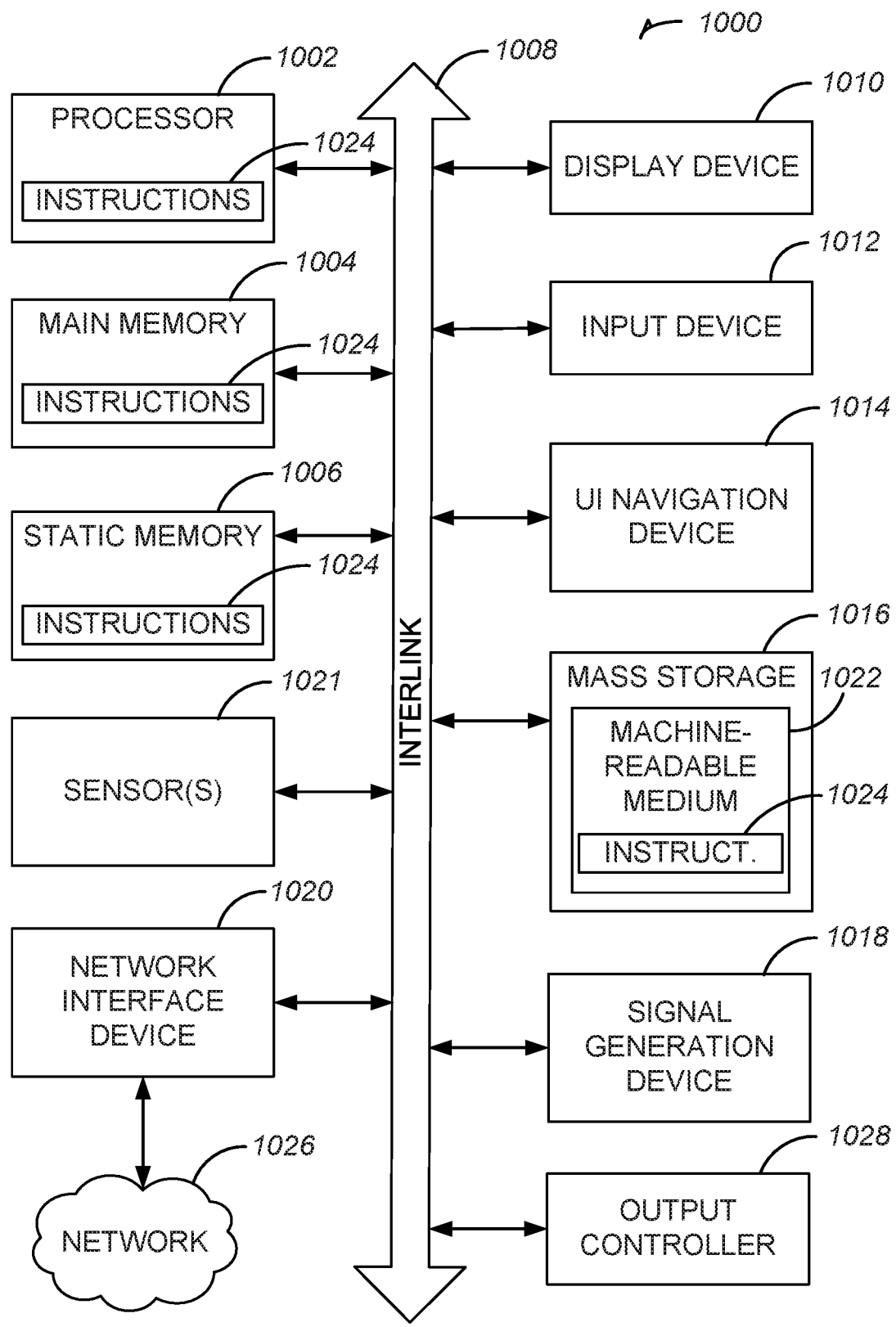
FIG. 10 illustrates a block diagram of an example machine upon which any one or more of the techniques discussed herein may perform, in accordance with some embodiments.

FIG. 10 illustrates a block diagram of an example machine 1000 upon which any one or more of the techniques (e.g., methodologies) discussed herein may perform. In alternative embodiments, the machine 1000 may operate as a standalone device or may be connected (e.g., networked) to other machines. In a networked deployment, the machine 1000 may operate in the capacity of a server machine, a client machine, or both in server-client network environments. In an example, the machine 1000 may act as a peer machine in peer-to-peer (P2P) (or other distributed) network environment. The machine 1000 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Machine (e.g., computer system) 1000 may include a hardware processor 1002 (e.g., a central processing unit (CPU), a graphics processing unit (GPU), a hardware processor core, or any combination thereof), a main memory 1004 and a static memory 1006, some or all of which may communicate with each other via an interlink (e.g., bus) 1008. The machine 1000 may further include a display unit 1010, an alphanumeric input device 1012 (e.g., a keyboard), and a user interface (UI) navigation device 1014 (e.g., a mouse). In an example, the display unit 1010, input device 1012 and UI navigation device 1014 may be a touch screen display. The machine 1000 may additionally include a storage device (e.g., drive unit) 1016, a signal generation device 1018 (e.g., a speaker), a network interface device 1020, and one or more sensors 1021, such as a global positioning system (GPS) sensor, compass, accelerometer, or other sensor. The machine 1000 may include an output controller 1028, such as a serial (e.g., Universal Serial Bus (USB), parallel, or other wired or wireless (e.g., infrared (IR), near field communication (NFC), etc.) connection to communicate or control one or more peripheral devices (e.g., a printer, card reader, etc.).

The storage device 1016 may include a machine readable medium 1022 on which is stored one or more sets of data structures or instructions 1024 (e.g., software) embodying or utilized by any one or more of the techniques or functions described herein. The instructions 1024 may also reside, completely or at least partially, within the main memory 1004, within static memory 1006, or within the hardware processor 1002 during execution thereof by the machine 1000. In an example, one or any combination of the hardware processor 1002, the main memory 1004, the static memory 1006, or the storage device 1016 may constitute machine readable media.

While the machine readable medium 1022 is illustrated as a single medium, the term "machine readable medium" may include a single medium or multiple media (e.g., a centralized or distributed database, and/or associated caches and servers) configured to store the one or more instructions 1024. The term "machine readable medium" may include any medium that is capable of storing, encoding, or carrying instructions for execution by the machine 1000 and that cause the machine 1000 to perform any one or more of the techniques of the present disclosure, or that is capable of storing, encoding or carrying data structures used by or associated with such instructions. Non-limiting machine readable medium examples may include solid-state memories, and optical and magnetic media.

The instructions 1024 may further be transmitted or received over a communications network 1026 using a transmission medium via the network interface device 1020 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, IEEE 802.16 family of standards known as WiMax®), IEEE 802.15.4 family of standards, peer-to-peer (P2P) networks, among others. In an example, the network interface device 1020 may include one or more physical jacks (e.g., Ethernet, coaxial, or phone jacks) or one or more antennas to connect to the communications network 1026. In an example, the network interface device 1020 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 1000, and includes digital or analog communications signals or other intangible medium to facilitate communication of such software.

An optical tracker, such as that illustrated in FIG. 7, may be a device configured with at least three marker arrays. A marker may be a reflective component (e.g., 702), and a marker array may be a configuration of at least three markers. An optical tracker may have many configurations. An optical tracker may have any number of marker arrays. Each marker array may have any number of markers. Depending on the configuration of the camera devices and system, a threshold may exist for the number of markers that are detected in order to determine a marker array. Similarly, a threshold may exist for the number of determined and detected marker arrays on an optical tracker in order to track the location and orientation of an optical tracker. Each marker array may be configured differently such that the system may identify each marker array separately on the optical tracker. For example, the markers in each marker array may have different reflective characteristics such that the system may identify the marker array based on the reflective brightness or color of the markers within the marker array. In another example, the markers in each marker array may be arranged in unique placements, such that each marker array has a unique arrangement of markers relative to each other. In yet another example, the marker arrays may be differentiated using an initialization procedure, where each array is registered or identified, and then tracked, such that even when the arrays are similarly arranged and have similar reflective characteristics, the arrays may be differentiated based on the initial positions and tracked locations. While the system may determine the position of the optical tracker based on the markers alone, by identifying a marker array, the system may determine the orientation of the optical tracker. By identifying a marker array, the system may identify which marker arrays are visible or not visible by each camera device and consequently perform calculations or adjustments for continuous tracking of the optical tracker.

In an example, the system may track the optical tracker with a single camera device when the system, through the images produced by the camera device, detects the three marker arrays on the optical tracker, such as that illustrated in FIG. 7. Detecting a marker array may vary for each system and scenario. For example, a system may be able to track an optical tracker when at least one marker from each marker array is detected, while in another example, the system may be able to track an optical tracker when at least two markers from each marker array are detected. In an example, where the marker array includes more than three markers, the system may be able to track based on some pre-defined subset of the full number of markers in the array.

In an example, the surgical field may have more than one camera device. In some examples, each camera device may include more than one sensor providing the ability to triangulate within each camera device. The system may utilize one camera device as a primary camera device. The primary camera device may be used by the system to track the optical tracker. When the primary camera device is not able to detect all three marker arrays on the optical tracker, the system may determine whether one or more of the secondary (non-primary) camera devices detects at least the marker arrays which are not detected by the primary camera device. For example, Camera A may be the primary camera device and track the optical tracker when Camera A has a view of marker arrays 1, 2, and 3 (e.g., all three marker arrays), though one or more may become obstructed. Marker array 3 is obstructed and thus Camera A only has a view of marker arrays 1 and 2 and information from Camera A alone is insufficient to track the optical tracker. The system may then check the view a secondary camera device has, such as Camera B. Camera B has a view of marker arrays 2 and 3. Between the combined views of Camera A and Camera B, all of the marker arrays of the optical tracker are detected by the system and the system may continue to determine the position of the optical tracker.

Figure 11:
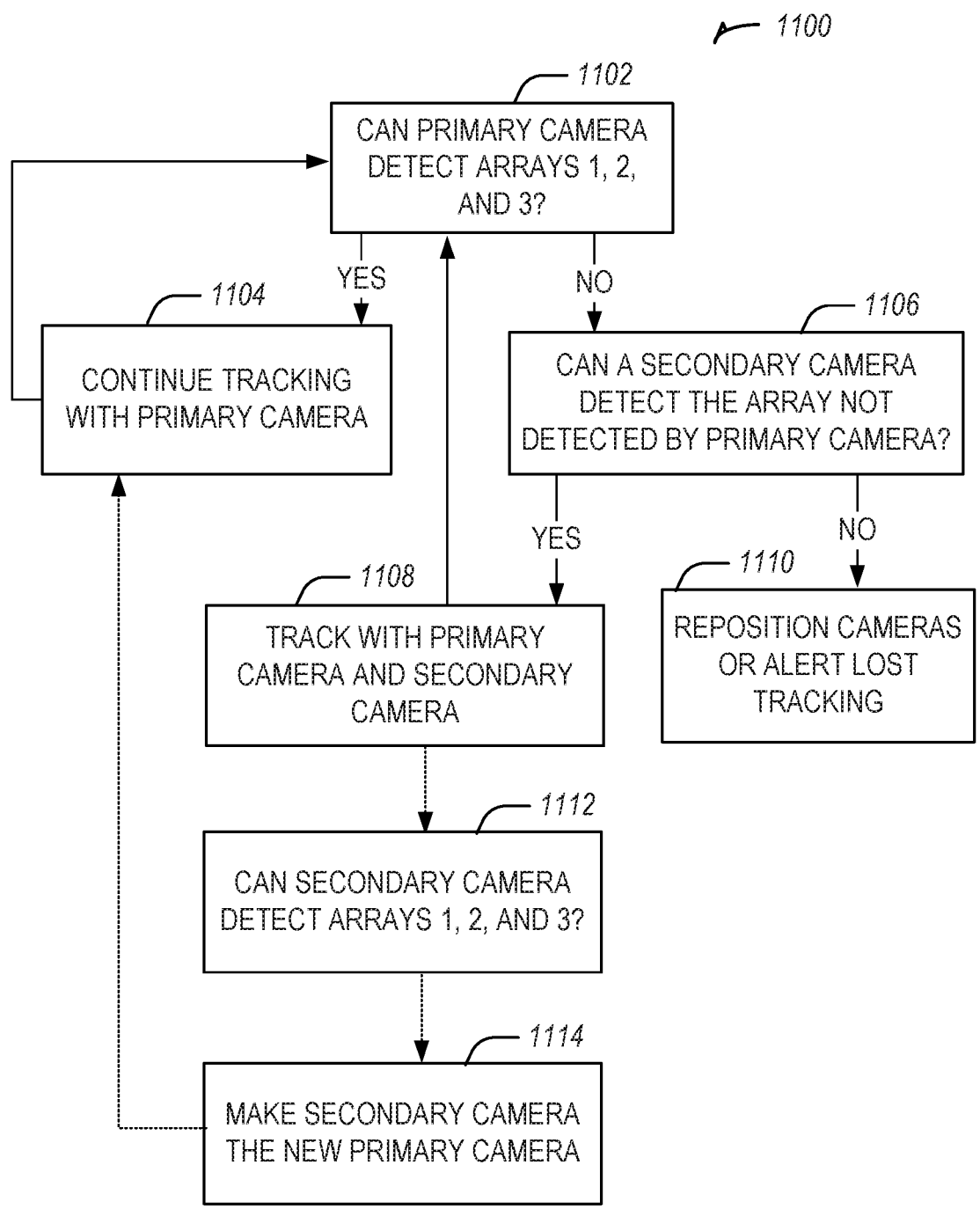
FIG. 11 illustrates a flowchart for determining when to switch from a primary camera device in a surgical field for tracking an optical tracker in accordance with some embodiments.

FIG. 11 illustrates a flowchart 1100 for determining when to switch from a primary camera device in a surgical field for tracking an optical tracker. The surgical field may have multiple camera devices capable of tracking an optical tracker. The system may designate a primary camera device for tracking the optical tracker and rely on designated secondary camera devices when the primary camera device cannot detect all the marker arrays on the optical tracker. At operation 1102, the system determines whether the primary camera device detects all three marker arrays (or some minimum subset of marker arrays). When the primary camera device detects all three marker arrays, then at operation 1104 the system continues to track the optical tracker with the primary camera device. The system may return to operation 1102 and confirm that the primary camera device is still detecting all three marker arrays. When the primary camera device cannot detect one or more of the three marker arrays, at operation 1106, the system may determine whether one of the secondary camera devices detects the marker array that the primary camera device is not able to detect. When one or more of the secondary camera devices do not detect all the marker arrays that the primary camera device is not able to detect, then at operation 1110, the system may reposition the camera devices or send an alert that the tracking of the optical tracker is lost. When one of the secondary camera devices detects the marker array that the primary camera device is not able to detect, then at operation 1108, the system may track the optical tracker with both the primary and secondary camera device. The system may return to operation 1102 to determine whether the primary camera device is able to detect all three marker arrays such that the system may return to tracking using just the primary camera device. In an optional set up, at operation 1108, the system may perform a check at operation 1112 and determine whether the secondary camera device detects all three marker arrays. When the secondary camera device detects all three marker arrays, then at operation 1114, the system may designate the secondary camera device as a new primary camera device. The system may then return to operation 1104 and continue tracking the optical tracker with the new primary camera device. As suggested by the discussion of technique 1100, the system can be configured to continuously switch out what is considered the primary camera device. The technique 1100 is discussed in terms of primary and secondary camera devices, but the technique can function with further "secondary" camera devices that can be tested serially or in parallel at operation 1112, for example.

Figure 12:
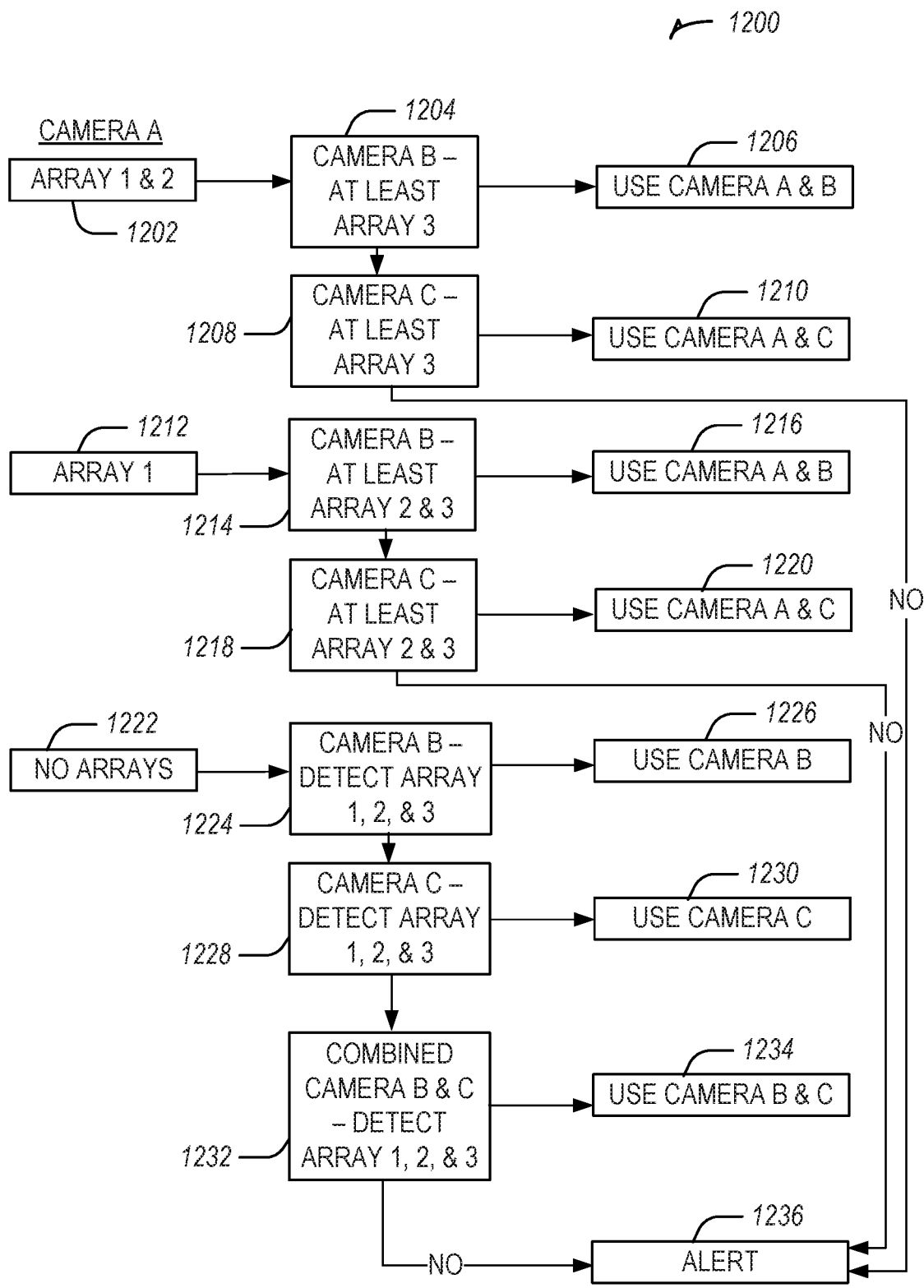
FIG. 12 illustrates a flowchart for a process of determining which camera device of a camera device array to use to track an optical tracker in accordance with some embodiments.

FIG. 12 illustrates a flowchart 1200 for a process of determining which camera devices to utilize when a primary camera device is not able to detect at least three marker arrays on an optical tracker. The flowchart 1200 illustrates an example scenario wherein to track the optical tracker, the camera devices need to detect at least three marker arrays on the optical tracker. As noted above, the techniques can be modified to apply to any minimum subset of total marker arrays considered necessary to properly track a particular optical tracker. Depending on the configuration of the surgical field camera system and the number of marker arrays on the optical tracker, the marker array detection threshold for tracking may vary. For example, depending on the configuration of the surgical field camera system, to track an optical tracker with three marker arrays, at least two of the marker arrays may need to be detected. In an example, depending on the configuration of the surgical field camera system, to track an optical tracker with five marker arrays, at least four of the marker arrays may need to be detected. The flowchart 1200 may be the process that occurs at operation 1106 of the flowchart 1100 from FIG. 11. In the scenario of flowchart 1200, Camera A is a primary camera device and Camera B and Camera C are secondary camera devices. At operation 1202, the system determines Camera A is detecting marker array 1 and 2, but not marker array 3 of the optical tracker. At operation 1204, the system determines whether Camera B is detecting at least marker array 3. When Camera B detects marker array 3, then at operation 1206, the system may utilize Camera A and B to track the optical tracker. When Camera B is not detecting at least marker array 3, then at operation 1208 the system may determine whether Camera C is detecting at least marker array 3. When Camera C detects marker array 3, then at operation 1210, the system may utilize Camera A and C to track the optical tracker. When Camera C does not detect at least marker array 3, then none of the camera devices are detecting marker array 3 and at operation 1236, the system may send an alert or move a camera device as the system may not be tracking the optical tracker.

At operation 1212, the system determines Camera A is detecting marker array 1, but not marker arrays 2 and 3 of the optical tracker. At operation 1214, the system determines whether Camera B is detecting at least marker arrays 2 and 3. When Camera B detects marker arrays 2 and 3, then at operation 1216, the system may utilize Camera A and B to track the optical tracker. When Camera B is not detecting at least marker arrays 2 and 3, then at operation 1218 the system may determine whether Camera C is detecting at least marker arrays 2 and 3. When Camera C detects marker arrays 2 and 3, then at operation 1220, the system may utilize Camera A and C to track the optical tracker. When Camera C is not detecting at least marker arrays 2 and 3, then none of the camera devices are detecting marker arrays 2 and 3 and at operation 1236, the system may send an alert or move a camera device as the system may not be tracking the optical tracker.

At operation 1222, the system determines Camera A is not detecting any marker arrays of the optical tracker. At operation 1224, the system determines whether Camera B is detecting marker arrays 1, 2, and 3. When Camera B detects marker arrays 1, 2, and 3, then at operation 1226, the system may utilize Camera B to track the optical tracker. The system may designate Camera B as the new primary camera device. When Camera B is not detecting marker arrays 1, 2, and 3, then at operation 1228 the system may determine whether Camera C is detecting marker arrays 1, 2, and 3. When Camera C detects marker arrays 1, 2, and 3, then at operation 1230, the system may utilize Camera C to track the optical tracker. The system may designate Camera C as the new primary camera device. When Camera C is not detecting marker arrays 1, 2, and 3, then at operation 1232, the system may determine whether Camera B and C combined detect arrays 1, 2, and 3. When Camera B and Camera C, combined, detect marker arrays 1, 2, and 3, then at operation 1234, the system may utilize Camera B and C to track the optical tracker. When Camera B and C do not detect marker arrays 1, 2, and 3, then none of the camera devices are detecting marker arrays 1, 2, and 3 and at operation 1236, the system may send an alert or move a camera device as the system may not be tracking the optical tracker.

Figure 13A:
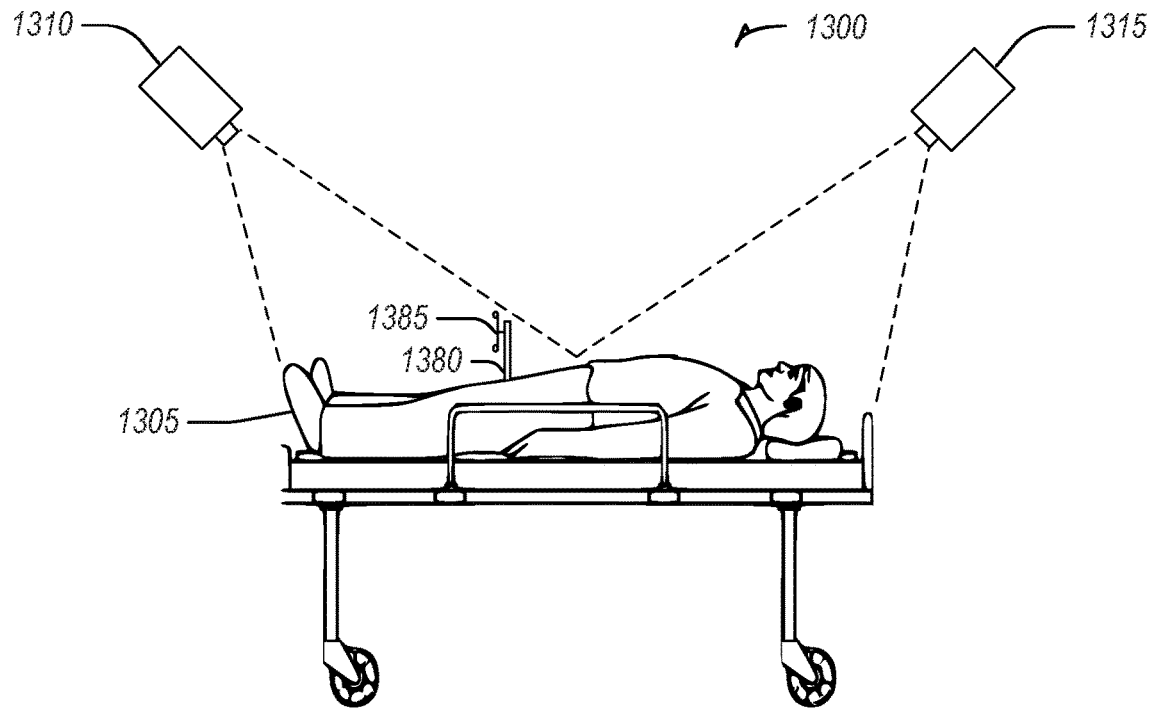
FIGS. 13A, 13B, and 13C illustrate camera device configurations for a surgical field in accordance with some embodiments.

FIG. 13A illustrates a camera device configuration 1300 for a surgical field in accordance with some embodiments. The operational field may include the whole body of a patient 1305, a portion of the patient 1305, or the patient 1305 and area surrounding the patient 1305. The camera device configuration 1300 may have two camera devices positioned in the surgical field to capture the operational field and supply captured images to the system for tracking objects with attached optical trackers. The camera device configuration 1300 may have a first camera device 1310 and a second camera device 1315. The camera devices may be positioned such that each camera device captures half of the operational field. For example, first camera device 1310 may be positioned to capture one half of the operational field, such as the part of the operational field that contains the lower half of the patient's 1305 body. Second camera device 1315 may be positioned to capture one half of the operational field, such as the part of the operational field that contains the upper half of the patient's 1305 body. Between the two camera devices, the whole operational field is captured with little or no overlap between the captured areas of each camera device. FIG. 13A includes an object 1380, such as a tool, surgical instrument, or body part connector, with an attached optical tracker 1385. In the example, first camera device 1310 captures and detects the optical tracker 1385, but second camera device 1315 does not. Camera device configuration 1300 illustrates a two camera device configuration, but any number of camera devices may be employed to fully capture the whole operational field. A body part connector may be a device used to secure an optical tracker to a part of the patient's body such that the connected optical tracker is utilized to track the position of the body part. The illustrations and examples provided describe a two camera device configuration as a means for describing a multiple camera device or more than one camera device configuration. The illustrations and examples provided include any camera device configuration of two or more camera devices. Additionally, as noted above, the discussed and illustrated camera devices can include multiple discrete cameras or sensors in fixed physical orientations to allow each camera device to provide triangulation information on an optical tracker.

The technique of tracking an object 1380 during a surgical operation may be used for multiple objects during the surgery. Tracking objects during a surgical operation may be utilized more as robots have an active role in performing surgeries. The system may track multiple parts of the patient's anatomy, multiple surgical tools, or the robot or parts of the robot. Thus, there may be multiple optical trackers employed during a surgical operation. With multiple optical trackers in use, the surgical field camera system may have difficulty determining the marker arrays for all the optical trackers from a set of images from a single camera device. Instead, the surgical field may be configured with two camera devices, such as first camera device 1310 and second camera device 1315, each positioned to capture an area of the surgical field such that a larger field of view is now captured. For example, the operational area or operational field of the surgical field, wherein the objects with connected optical trackers may be in use, may be divided in half such that each camera device has a field of view encompassing one half of the operational field.

Utilizing two camera devices, first camera device 1310 and second camera device 1315, to each capture half the field of view allows for the capture of a larger total field of view. The detection and tracking of the optical trackers, such as optical tracker 1385, may be divided between each camera device. In an embodiment, a computer may process the tracking image data for each camera device separately. In an embodiment, each camera device may be connected to a dedicated separate computer system for processing the tracking image data. For example, first camera device 1310 may be connected to a first computer system for processing tracking image data from first camera device 1310 and second camera device 1315 may be connected to a second computer system for processing tracking image data from second camera device 1315. The captured images along with the tracking data from each camera device may be composited to create the total field of view for the operational field and produce location and positional data for each optical tracker 1385.

Figure 13B:
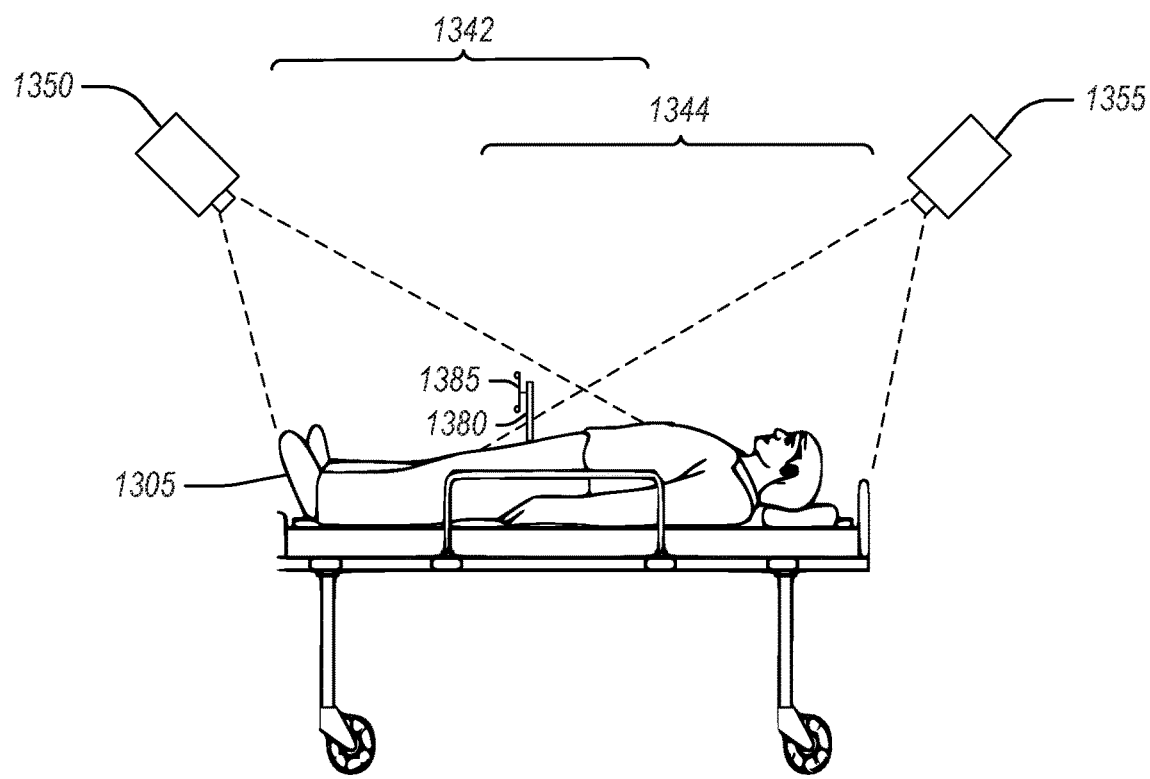

FIG. 13B illustrates a camera device configuration 1340 for a surgical field in accordance with some embodiments. The camera device configuration 1340 may have two camera devices positioned in the surgical field to capture the operational field and supply captured images to the surgical field camera system for tracking objects with attached optical trackers. The camera device configuration 1340 may have a first camera device 1350 and a second camera device 1355. The camera devices may be positioned such that each camera device captures a majority, but not all of the operational field. The captured area for each camera device overlaps with a portion of the captured area for the other camera device. For example, the first camera device 1350 may be positioned to capture a majority of the operational field, such as a first field of view 1342 capturing the part of the operational field that contains the legs and torso of the patient's 1305 body. Second camera device 1355 may be positioned to capture a majority of the operational field, such as second field of view 1344 capturing the part of the operational field that contains the head, torso, and upper leg of the patient's 1305 body. Between the two camera devices, first field of view 1342 and second field of view 1344 capture the whole operational field with overlap for a priority area of the operational field. The overlap portion may be an area where the majority of the optical trackers may be utilized and the areas captured by one camera device may be an area where a minority of the optical trackers are utilized. Configuring the camera devices to overlap may allow for optical trackers to be within the field of view of each camera device, although assigned to only one of the camera devices.

In the illustrated example for camera device configuration 1340, the object 1380 with attached optical tracker 1385 may be assigned to first camera device 1350 for tracking. The object 1380 is partially within the second field of view 1344 for second camera device 1355. However, the optical tracker 1385 is not within the second field of view 1344 for second camera device 1355. The optical tracker 1385 is within the first field of view 1342 for first camera device 1350.

Figure 13C:
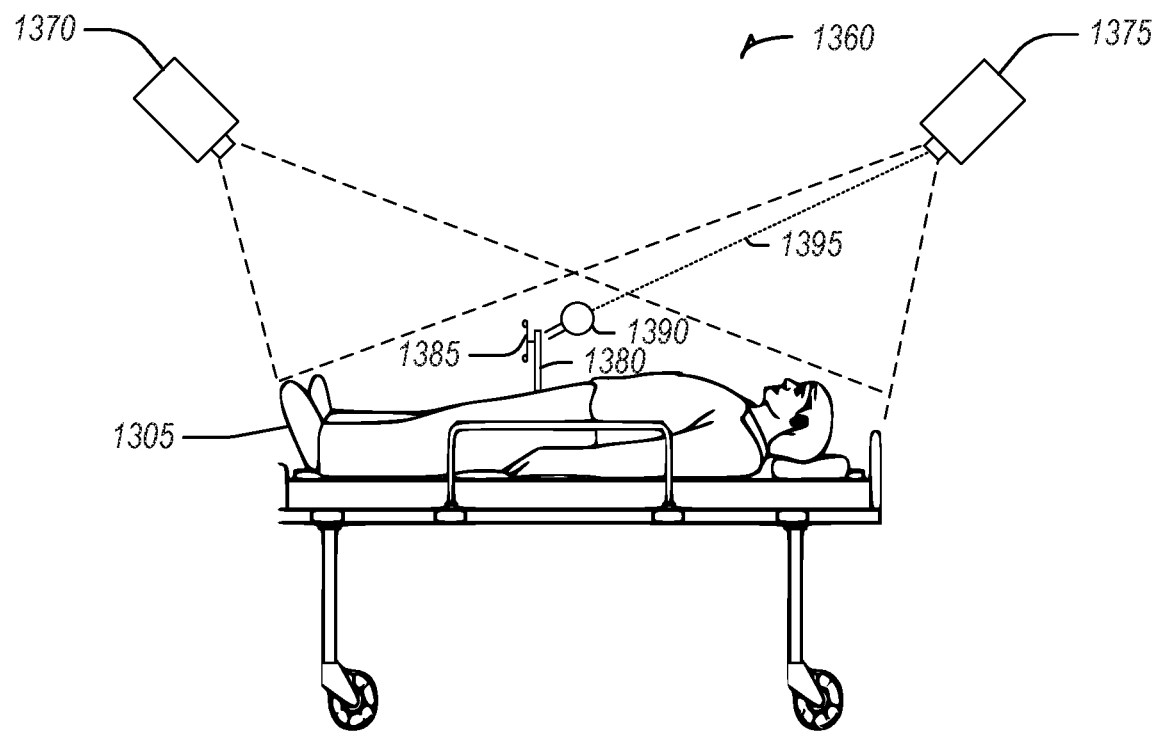

FIG. 13C illustrates a camera device configuration 1360 for a surgical field in accordance with some embodiments. The camera device configuration 1360 may have two camera devices positioned in the surgical field to capture the operational field and supply captured images to the system for tracking objects with attached optical trackers. The camera device configuration 1360 may have a first camera device 1370 and a second camera device 1375. The camera devices may be positioned such that each camera device captures all of the operational field. The captured area for each camera device overlaps with the captured area for the other camera device. For example, first camera device 1370 may be positioned to capture all of the operational field, such as all of the patient's 1305 body. When the entirety of the operational field is a portion of the patient's 1305 body, such as the leg of the patient 1305, then the first camera device 1370 may be positioned to capture the leg. Second camera device 1375 may be positioned to capture all of the operational field as well. Both the camera devices may completely overlap and each capture the whole operational field.

An object 1380, such as an instrument or tool, utilized during a surgical procedure in the operational field may have an optical tracker 1385 attached to it. The first camera device 1370 and second camera device 1375 may capture optical trackers, such as optical tracker 1385, so that the position and orientation of the object 1380 may be tracked during a surgical procedure. In an example, the optical tracker 1385 may be positioned on the instrument such that the position of the object 1380 in the operational field results in the marker arrays of the optical tracker 1385 only being visible to the view of one camera device, such as first camera device 1370. For example, robot arm 1390 may block the line of sight 1395 for second camera device 1375 to the optical tracker 1385. The system may assign the optical tracker 1385 to the first camera device 1370. The second camera device 1375 may be used to capture the optical tracker 1385, should the marker arrays be visible to second camera device 1375. When multiple optical trackers are present in the operational field and it is known only one of the camera devices may have a clear line of site to the optical tracker 1385, the assignment of an optical tracker to a camera device reduces the processing required from one captured image to the next for tracking the particular optical tracker.

The surgical field may be configured with two camera devices, such as first camera device 1370 and second camera device 1375, to capture the operational field, where the camera devices are positioned to have completely overlapping field of views, such as camera device configuration 1360. Such a configuration may be used when occlusion of the optical trackers may have a high probability or prevention of lost tracking is high priority. Each camera device may be assigned a subset of the optical trackers in the operational field. Both camera devices may be assigned to track all the optical trackers in the operational field. The system may analyze image information produced from each camera device and to determine which camera device has the clearest line of sight for each optical tracker and designate optical trackers to the camera devices accordingly. When the system determines a camera device has a less than clear or occluded line of sight to an optical tracker that was designated to that camera device, the system may utilize the other camera device to maintain tracking of that optical tracker.

Figure 14:
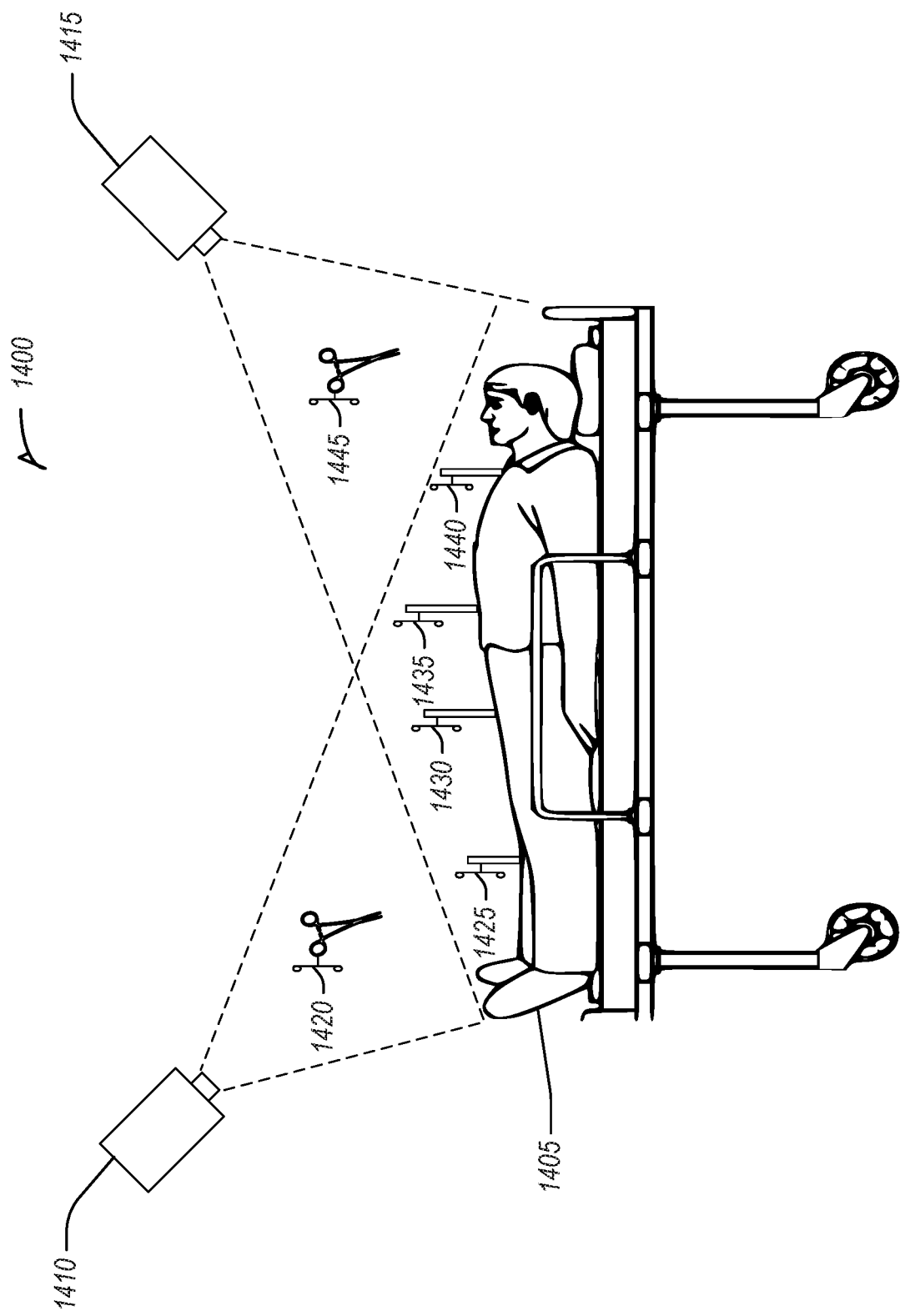
FIG. 14 illustrates a camera device configuration for a surgical field in accordance with some embodiments.

FIG. 14 illustrates a camera device configuration 1400 for a surgical field in accordance with some embodiments. The overlapping field of view camera device configuration may have a subset of optical trackers that are tracked by both camera devices, first camera device 1410 and second camera device 1415. Of the optical trackers present in the operational field, a primary or essential optical tracker, or set of primary optical trackers, may be identified, which may then be assigned to be tracked by both camera devices. The remaining optical trackers may be assigned to only one of the camera devices in the surgical field. For example, there may be six optical trackers employed in the surgical field. First optical tracker 1420 and sixth optical tracker 1445 may be identified as secondary optical trackers. Second optical tracker 1425, third optical tracker 1430, fourth optical tracker 1435, and fifth optical tracker 1440 may be identified as the primary optical trackers and may be located in the overlapped field of view area of the first camera device 1410 and second camera device 1415. Second optical trackers 1425, third optical tracker 1430, fourth optical tracker 1435, and fifth optical tracker 1440 may be tracked by both camera devices. First optical tracker 1420 may be assigned to only be tracked by the first camera device and sixth optical tracker 1445 may be assigned to only be tracked by the second camera device. In an embodiment, the optical trackers may be attached to an instrument or tool such that the optical tracker is on the side of the instrument or tool. This positioning may result in the marker array side of the tracker being visible to one camera device, but the underside of the optical tracker, or non-marker array side, visible to the other camera device. In such an embodiment, the optical tracker may be assigned to the camera device with the visibility to the marker array side of the optical tracker.

Each camera device may be assigned a subset of the total set of optical trackers. This may reduce the processing necessary for each produced image to determine the location of the optical trackers in each image. When the image processing computer is aware of which optical trackers may be present in each produced image, the image processing computer may filter out unnecessary image noise which is not a marker for an optical tracker. For example, when the surgical field, such as FIG. 14, has six different optical trackers, the first camera device 1410 may be assigned to track the first three optical trackers and the second camera device 1415 may be assigned to track the second three optical trackers. In another example, before the surgical procedure begins, three optical trackers may be assigned and positioned within the first camera device's 1410 field of view and the three other optical trackers may be assigned and positioned within the second camera device's 1415 field of view.

The system may take aspects from the image information produced by each camera device to create a composite total view of the operational field. The composite total view may be analyzed to determine the location of each optical tracker. For a particular optical tracker, one of the camera devices may only have a line of sight to a portion of the optical tracker's marker arrays and the other camera device may only have a line of sight to a portion of the optical tracker's marker arrays. The composite total view may combine aspects from each camera device's field of view to locate all the marker arrays for the particular optical tracker and determine the location of the optical tracker. Patching together aspects from both camera devices to form one composite total view may be performed for multiple optical trackers present in the surgical field. For example, the system may receive image information from both camera devices, and construct a composite image as one total field of view for the operational field. The composite image may include all of the markers detected within the field of view, wherein the composite image retains only one marker image for any marker that is visible in both captured images. The system may analyze the composite image to locate each optical tracker and determine the location and position of each optical tracker in the surgical field. The system may perform this image composition, analysis, and location determination for each set of captured images received from the two camera devices to track the optical trackers.

The system may use past frame data to determine the location of the optical tracker when the line of sight to the optical tracker by a camera device has become obscured. In the surgical field, people and objects are moving around as the surgical procedure takes place. When the system determines a camera device no longer has a view of an optical tracker, the system may use past frame data to determine the location of the optical tracker. For example, when the tracker is no longer detected, the system may analyze the past frame data and determine for a predetermined number of frames the optical tracker has stayed stationary. This may indicate that the optical tracker did not move, but that something has blocked the view of the camera device. Thus the system may have the camera device continue to focus on the position the optical tracker was last known, until the view is no longer blocked. During this time the system may have another camera device determine whether it can locate the optical tracker, when another camera device is available. In another example, when the system determines the optical tracker is no longer detected, the system may analyze a predetermined number of past frames of data to determine the optical tracker was moving and may have moved out of the view of the camera device. The system may use the movement to obtain trajectory data to reposition the camera device or utilize a different camera device to locate the optical tracker, wherein the system utilizes the trajectory data to determine which camera device has the best vantage point of the current location of the optical tracker. In an example, a system utilizing three or more camera devices, the trajectory data may be utilized to assist the system in identifying the next camera device to check or attempt to utilize to track the optical tracker. For example, the system can determine, when camera device 1 loses sight of the optical tracker, which of the adjacent camera device 2 or camera device 3 is most likely to have the optical tracker in view based on knowledge of the field of view coverage of camera device 2 and camera device 3 as well as the trajectory information from past frame of camera device 1.

Figure 15:
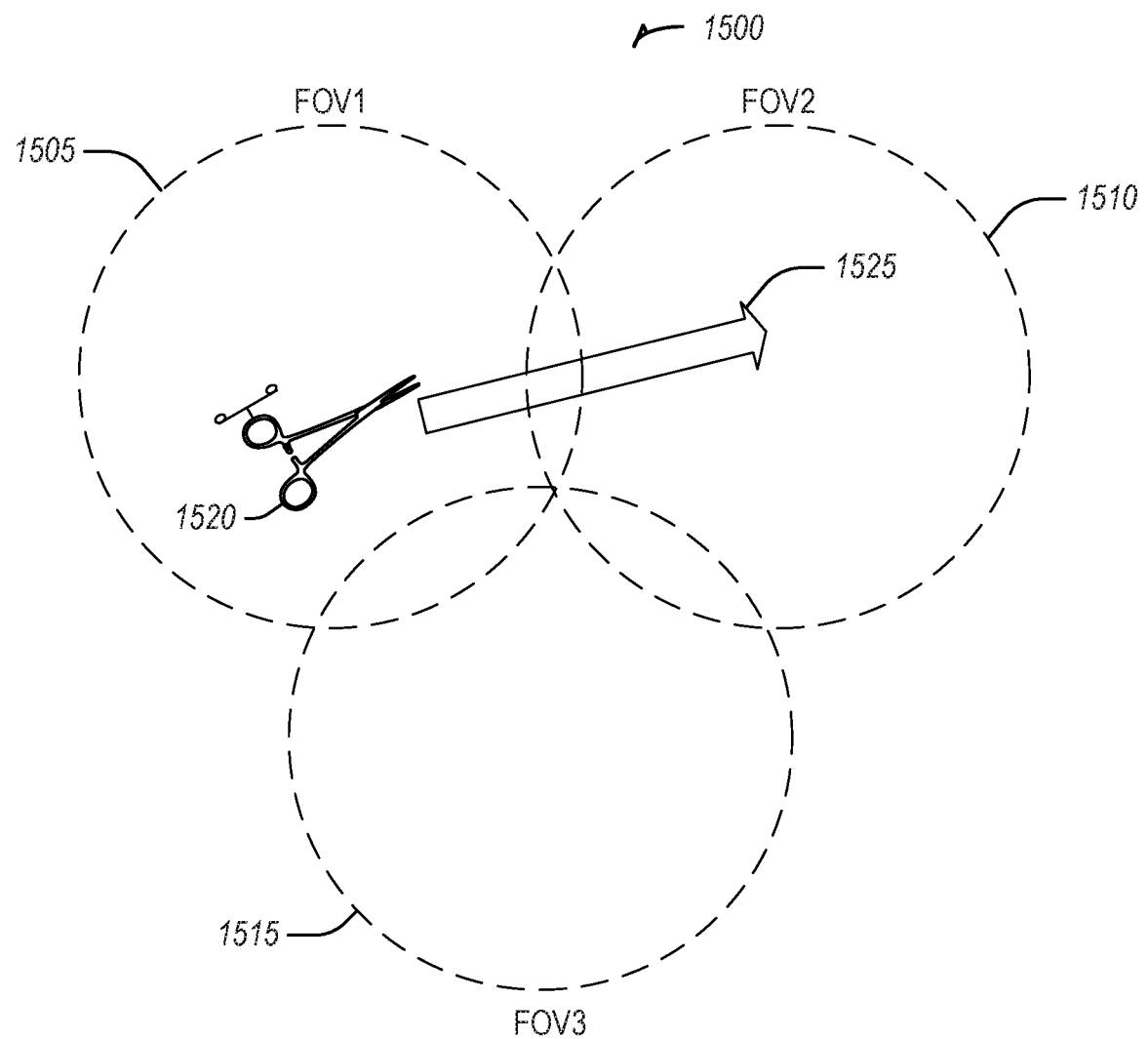
FIG. 15 illustrates a multiple camera device field of view for tracking an object in accordance with some embodiments.

FIG. 15 illustrates a multiple camera device field of view 1400 for tracking an object in accordance with some embodiments. The multiple camera device field of view 1400 depicts an example field of view for three camera devices, wherein each field of view corresponds to a different camera device. The total field of view (FOV) comprises FOV1 1505, FOV2 1510, and FOV3 1515. As illustrated in the example, the FOV1 1505, FOV2 1510, and FOV3 1515 may overlap. The camera device corresponding to FOV1 1505 may capture an object for tracking, such as instrument 1520 with an attached optical tracker. The instrument 1520 may be moved in the surgical field, this is illustrated by trajectory arrow 1525.

As indicated by trajectory arrow 1525, the instrument 1520 may move from FOV1 1505 to FOV2 1510. As the instrument 1520 begins to move in the direction indicated by the trajectory arrow 1525, the system may utilize this captured movement information to determine the trajectory of the instrument 1520. Based on the calculated trajectory, the system may determine if the instrument 1520 may move out of the field of view for the camera device currently tracking the instrument 1520. The system may determine the instrument may move out of the current field of view and determine which field of view of the other camera devices the instrument 1520 may enter. As the instrument 1520 edge of the current field of view, the system may transition to another camera device for tracking the instrument 1520. For example, as instrument 1520 begins to move in the direction indicated by trajectory arrow 1525, the system may determine the trajectory of the instrument 1525. As illustrated, the system may determine, based on the determined trajectory, that the instrument 1520 may enter FOV2 1510 and not FOV3 1515. Based on this determination, as the instrument 1520 approaches the edge of FOV1 1505, such as the overlap area of FOV1 1505 and FOV2 1510, the system may transition the tracking of the instrument 1520 to the camera device associated with FOV2 1510.

The camera devices in the surgical field may include an identifying mark on the housing of the camera device such that other camera devices in the surgical field may identify the camera device. This may include any camera device in the surgical field, such as stationary camera devices attached to the wall or ceiling, camera devices incorporated into an AR headset, moveable camera devices such as on a track, and camera devices attached to a robot. The identifying mark may be conspicuous and well defined such that another camera device may easily view the marking for identification determination by the system. The identifying mark may be a QR code or block style numbers, an optical tracker, a digital identifier, or the like. The camera devices may also include a wireless network interface, such as Bluetooth, and each camera device may be identified through near-field communication (NFC) detection of a radio frequency identifier (RFID).

Through identification of the other camera devices in the surgical field, the system may determine the location of the camera devices such that the system may then determine the location of an object within the field of view for the camera devices. This may be applicable for use with camera device incorporated into an AR headset, as determining a precise location in a small area, such as the surgical field, of the operator wearing the AR headset may be difficult, even with location sensors. In an example embodiment, the surgical field may have two stationary camera devices, Camera A and Camera B. Camera A and Camera B are stationary, and their location in the surgical field is known. The surgical field may also have a camera device, Camera C, incorporated into an AR headset. When the operator wearing the headset moves about the surgical field, the location of Camera C may change. In an example, neither Camera A nor Camera B may have a clear view of the tracked object. However, Camera C, may have a clear view as the operator has a direct view of the object. The system may determine the position of Camera C with an identifying mark, optical tracker, digital identifier, or the like, placed on Camera C, such that Camera A, Camera B, or both may provide information for the system to identify Camera C and determine its location. Using the known location and position of Camera C, the system may determine the location of the tracked object detected by Camera C.

Example 1 is a system for tracking an object within a surgical field, the system comprising: a mesh of cameras distributed around the surgical field, the mesh of cameras including at least three cameras, wherein each camera in the mesh of cameras is in a known position and orientation relative to the surgical field; a computing system communicatively coupled to the mesh of cameras, the computing system including a processor and a memory device, the memory device including instructions that, when executed by the processor, cause the computing system to: receive synchronized image captures from the at least three cameras in the mesh of cameras wherein at least a portion of the synchronized image captures include, information indicative of a position and orientation of a tracked object within the surgical field; analyze the synchronized image captures, to detect that a sight line from at least one camera of the at least three cameras to the tracked object is at least partially obstructed; generate tracking data for the tracked object, wherein the tracking data is generated from information extracted from at least two image captures of at least two cameras of the at least three cameras, the tracking data generated without using an image capture corresponding to the at least one camera with the sight line at least partially obstructed; determine, from the tracking data, a position and an orientation of the tracked object within a virtual three-dimensional coordinate system; and output the position and the orientation of the tracked object.

In Example 2, the subject matter of Example 1 includes, wherein the instructions to analyze the synchronized image captures further includes instructions that cause the computing system to: determine a tracking strength indicator for each image in the synchronized image captures; and utilize each image of the synchronized image captures that includes a tracking strength indicator that exceeds a predetermined threshold.

In Example 3, the subject matter of Example 2 includes, wherein the instructions to determine the tracking strength indicator include instructions that determine how much of an aspect of the tracked object is occluded in each image of the synchronized image captures.

In Example 4, the subject matter of Example 3 includes, wherein: the tracked object includes a tracking frame with a plurality of tracking markers; and determining how much of the aspect of the tracked object is occluded includes determining how many of the plurality of tracking markers are visible in each image of the synchronized image captures.

In Example 5, the subject matter of Examples 1-4 includes, wherein: the mesh of cameras includes at least two pairs of infrared cameras, each pair of infrared cameras including two infrared cameras fixedly positioned in a respective housing; and the tracked object includes a plurality of infrared-reflective marker components arranged rigidly in a specified orientation to one another, the plurality of infrared-reflective marker components being attachable as a rigid structure to a surgical instrument or an anatomy of a patient.

In Example 6, the subject matter of Example 5 includes, wherein: the mesh of cameras includes at least three pairs of infrared cameras; and the computing system is configured to generate the tracking data using synchronized image captures from any two of the at least three pairs of infrared cameras.

In Example 7, the subject matter of Examples 1-6 includes, a display configured to receive and display the position and the orientation of the tracked object.

In Example 8, the subject matter of Examples 1-7 includes, a controller configured to: receive the position and the orientation of the tracked object; and control a surgical tool such that the surgical tool is activated only when the position and orientation of the surgical tool is within a specified range of positions and orientations.

In Example 9, the subject matter of Examples 1-8 includes, a surgical robot configured to: receive the position and the orientation of the tracked object; and actuate a surgical tool in response to the position and the orientation of the tracked object.

In Example 10, the subject matter of Examples 1-9 includes, wherein the instructions further cause the computing system to add an additional camera to the mesh of cameras, and receive synchronized image captures from the additional camera.

In Example 11, the subject matter of Example 10 includes, wherein the instructions further cause the computing system to calibrate the additional camera including determining a position and an orientation of the additional camera relative to a virtual three-dimensional coordinate system that encompasses a working portion of the surgical field.

In Example 12, the subject matter of Example 11 includes, wherein the instructions to calibrate the additional camera further cause the computing system to measure a position and an orientation of the additional camera relative to at least one other camera of the mesh of cameras.

In Example 13, the subject matter of Examples 1-12 includes, a wearable headset configured to display data corresponding to the position and the orientation of the tracked object, overlaid with at least one of the tracked object, an instrument attached to the tracked object, or an anatomical element attached to the tracked object.

In Example 14, the subject matter of Example 13 includes, wherein the wearable headset includes one of the at least three cameras in the mesh of cameras.

Example 15 is a method comprising: a processor in communication with memory storing instructions for tracking an object within a surgical field, which when executed by the processor, cause the processor to: receiving synchronized image captures from a plurality of cameras in a mesh of cameras, wherein the plurality of cameras includes, at least three cameras distributed around the surgical field, the received synchronized image captures including a first image from a first camera, a second image from a second camera, and a third image from a third camera, wherein at least a portion of the synchronized image captures include information indicative of a position and orientation of a tracked object within the surgical field; analyzing the synchronized image captures, including the first image, the second image, and the third image, to generate tracking data for the tracked object, wherein the tracking data is generated from information extracted from at least two of the first image, the second image, and the third image; determining, based on the tracking data, a position and an orientation of the tracked object within a virtual three-dimensional coordinate system; and outputting the position and the orientation of the tracked object.

In Example 16, the subject matter of Example 15 includes, determining a tracking strength indicator for each image in the synchronized image captures; and utilizing each image of the synchronized image captures that includes a tracking strength indicator that exceeds a predetermined threshold.

In Example 17, the subject matter of Example 16 includes, wherein determining the tracking strength indicator includes determining how much of an aspect of the tracked object is occluded in each image of the synchronized image captures.

In Example 18, the subject matter of Examples 16-17 includes, wherein: the tracked object includes a tracking frame with a plurality of tracking markers; and determining how much of the aspect of the tracked object is occluded includes determining how many of the plurality of tracking markers are visible in each image of the synchronized image captures.

In Example 19, the subject matter of Examples 16-18 includes, a surgical robot configured to: receive the position and the orientation of the tracked object with a surgical robot; and with the surgical robot, actuating a surgical tool in response to the position and the orientation of the tracked object.

In Example 20, the subject matter of Examples 16-19 includes, adding an additional camera to the mesh of cameras; and receiving synchronized image captures from the additional camera.

Example 21 is at least one non-transitory machine-readable medium including instructions for tracking an object within a surgical field, which when executed by a processor, cause the processor to: receive synchronized image captures from a plurality of cameras in a mesh of cameras, wherein the plurality of cameras includes, at least three cameras distributed around the surgical field, the received synchronized image captures including a first image from a first camera, a second image from a second camera, and a third image from a third camera, wherein at least a portion of the synchronized image captures include information indicative of a position and orientation of a tracked object within the surgical field; analyze the synchronized image captures, including the first image, the second image, and the third image, to generate tracking data for the tracked object, wherein the tracking data is generated from information extracted from at least two of the first image, the second image, and the third image; determine, based on the tracking data, a position and an orientation of the tracked object within a virtual three-dimensional coordinate system; and output the position and the orientation of the tracked object.

In Example 22, the subject matter of Example 21 includes, wherein the instructions to analyze the synchronized image captures further includes instructions that cause the processor to: determine a tracking strength indicator for each image in the synchronized image captures; and utilize each image of the synchronized image captures that includes a tracking strength indicator that exceeds a predetermined threshold.

In Example 23, the subject matter of Example 22 includes, wherein the instructions to determine the tracking strength indicator include instructions that determine how much of an aspect of the tracked object is occluded in each image of the synchronized image captures.

In Example 24, the subject matter of Example 23 includes, wherein: the tracked object includes a tracking frame with a plurality of tracking markers; and determining how much of the aspect of the tracked object is occluded includes determining how many of the plurality of tracking markers are visible in each image of the synchronized image captures.

In Example 25, the subject matter of Examples 21-24 includes, wherein: the mesh of cameras includes at least two pairs of infrared cameras, each pair of infrared cameras including two infrared cameras fixedly positioned in a respective housing; and the tracked object includes a plurality of infrared-reflective marker components arranged rigidly in a specified orientation to one another, the plurality of infrared-reflective marker components being attachable as a rigid structure to a surgical instrument or an anatomy of a patient.

In Example 26, the subject matter of Example 25 includes, wherein: the mesh of cameras includes at least three pairs of infrared cameras; and the computing system is configured to generate the tracking data using synchronized image captures from any two of the at least three pairs of infrared cameras.

In Example 27, the subject matter of Examples 21-26 includes, a display configured to receive and display the position and the orientation of the tracked object.

In Example 28, the subject matter of Examples 21-27 includes, a controller configured to: receive the position and the orientation of the tracked object; and control a surgical tool such that the surgical tool is activated only when the position and orientation of the surgical tool is within a specified range of positions and orientations.

In Example 29, the subject matter of Examples 21-28 includes, a surgical robot configured to: receive the position and the orientation of the tracked object; and actuate a surgical tool in response to the position and the orientation of the tracked object.

In Example 30, the subject matter of Examples 21-29 includes, wherein the instructions further cause the processor to add an additional camera to the mesh of cameras, and receive synchronized image captures from the additional camera.

In Example 31, the subject matter of Example 30 includes, wherein the instructions further cause the processor to calibrate the additional camera including determining a position and an orientation of the additional camera relative to a virtual three-dimensional coordinate system that encompasses a working portion of the surgical field.

In Example 32, the subject matter of Example 31 includes, wherein the instructions to calibrate the additional camera further cause the processor to measure a position and an orientation of the additional camera relative to at least one other camera of the mesh of cameras.

In Example 33, the subject matter of Examples 31-32 includes, a wearable headset configured to display data corresponding to the position and the orientation of the tracked object, overlaid with at least one of the tracked object, an instrument attached to the tracked object, or an anatomical element attached to the tracked object.

In Example 34, the subject matter of Example 33 includes, wherein the wearable headset includes one of the at least three cameras in the mesh of cameras.

Example 35 is at least one machine-readable medium including instructions that, when executed by processing circuitry, cause the processing circuitry to perform operations to implement of any of Examples 1-34.

Example 36 is an apparatus comprising means to implement of any of Examples 1-34.

Example 37 is a system to implement of any of Examples 1-34.

Example 38 is a method to implement of any of Examples 1-34.

Method examples described herein may be machine or computer-implemented at least in part. Some examples may include a computer-readable medium or machine-readable medium encoded with instructions operable to configure an electronic device to perform methods as described in the above examples. An implementation of such methods may include code, such as microcode, assembly language code, a higher-level language code, or the like. Such code may include computer readable instructions for performing various methods. The code may form portions of computer program products. Further, in an example, the code may be tangibly stored on one or more volatile, non-transitory, or non-volatile tangible computer-readable media, such as during execution or at other times. Examples of these tangible computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

What is claimed is:

1. A system for tracking an object within a surgical field, the system comprising:
   a mesh of cameras distributed around the surgical field, the mesh of cameras including at least three pairs of infrared cameras, wherein each camera in the mesh of cameras is in a known position and orientation relative to the surgical field and each pair of infrared cameras includes two infrared cameras fixedly positioned in a respective housing;
   a computing system communicatively coupled to the mesh of cameras, the computing system including a processor and a memory device, the memory device including instructions that, when executed by the processor, cause the computing system to:
   receive synchronized image captures from any two of the at least three pairs of infrared cameras in the mesh of cameras wherein at least a portion of the synchronized image captures include information indicative of a position and orientation of a tracked object within the surgical field, wherein the tracked object includes a plurality of infrared-reflective marker components arranged rigidly in a specified orientation to one another, the plurality of infrared-reflective marker components being attachable as a rigid structure to a surgical instrument or an anatomy of a patient;
   analyze the synchronized image captures, to detect that a sight line from at least one camera of the at least three pairs of infrared cameras to the tracked object is at least partially obstructed, the detection based on a respective synchronized image capture including insufficient tracking strength indicator information;
   generate tracking data for the tracked object using only data captured by cameras of the mesh of cameras, wherein the tracking data is generated from information extracted from at least two image captures, having sufficient tracking strength indicator information that transgresses a pre-determined threshold, of at least two pairs of infrared cameras of the at least three pairs of infrared cameras, the tracking data generated without using an image capture corresponding to the at least one camera with the sight line at least partially obstructed, wherein the pre-determined threshold is set to avoid false positive tracking identifications;
   determine, from the tracking data, a position and an orientation of the tracked object within a virtual three-dimensional coordinate system; and output the position and the orientation of the tracked object.

2. The system of claim 1, wherein the instructions to analyze the synchronized image captures further includes instructions that cause the computing system to:
- determine a tracking strength indicator for each image in the synchronized image captures; and
- utilize each image of the synchronized image captures that includes a tracking strength indicator that exceeds the predetermined threshold.

3. The system of claim 2, wherein the instructions to determine the tracking strength indicator include instructions that determine how much of an aspect of the tracked object is occluded in each image of the synchronized image captures.

4. The system of claim 3, wherein:
- the tracked object includes a tracking frame with the plurality of infrared-reflective marker components; and
- determining how much of the aspect of the tracked object is occluded includes determining how many of the plurality of infrared-reflective marker components are visible in each image of the synchronized image captures.

5. The system of claim 1, further comprising a display configured to receive and display the position and the orientation of the tracked object.

6. The system of claim 1, further comprising a controller configured to:
- receive the position and the orientation of the tracked object; and
- control a surgical tool such that the surgical tool is activated only when the position and orientation of the surgical tool is within a specified range of positions and orientations.

7. The system of claim 1, further comprising a surgical robot configured to:
- receive the position and the orientation of the tracked object; and
- actuate a surgical tool in response to the position and the orientation of the tracked object.

8. The system of claim 1, wherein the instructions further cause the computing system to add an additional camera to the mesh of cameras, and receive synchronized image captures from the additional camera.

9. The system of claim 8, wherein the instructions further cause the computing system to calibrate the additional camera including determining a position and an orientation of the additional camera relative to a virtual three-dimensional coordinate system that encompasses a working portion of the surgical field.

10. The system of claim 9, wherein the instructions to calibrate the additional camera further cause the computing system to measure a position and an orientation of the additional camera relative to at least one other camera of the mesh of cameras.

11. The system of claim 1, further comprising a wearable headset configured to display data corresponding to the position and the orientation of the tracked object, overlaid with at least one of the tracked object, an instrument attached to the tracked object, or an anatomical element attached to the tracked object.

12. The system of claim 11, wherein the wearable headset includes one of the at least three pairs of infrared cameras in the mesh of cameras.

13. A method comprising:
- a processor in communication with memory storing instructions for tracking an object within a surgical field, which when executed by the processor, cause the processor to:
  - receiving synchronized image captures from a plurality of cameras in a mesh of cameras, wherein the plurality of cameras includes at least two pairs of at least three pairs of infrared cameras distributed around the surgical field in the mesh of cameras wherein each pair of infrared cameras includes two infrared cameras fixedly positioned in a respective housing, the received synchronized image captures including a first set of images from a first pair of infrared cameras, a second set of images from a second pair of infrared cameras, and a third set of images from a third pair of infrared cameras, wherein at least a portion of the synchronized image captures include information indicative of a position and orientation of a tracked object within the surgical field, wherein the tracked object includes a plurality of infrared-reflective marker components arranged rigidly in a specified orientation to one another, the plurality of infrared-reflective marker components being attachable as a rigid structure to a surgical instrument or an anatomy of a patient;
  - analyzing the synchronized image captures, including identifying tracking strength indicator information for each of the first set of images, the second set of images, and the third set of images and detecting that at least one of the synchronized image captures includes insufficient tracking strength indicator information, to generate tracking data for the tracked object using only data captured by cameras of the mesh of cameras, wherein the tracking data is generated from information extracted from at least two of the first set of images, the second set of images, and the third set of images, the at least two having sufficient tracking strength indicator information, that transgresses a pre-determined threshold, wherein the pre-determined threshold is set to avoid false positive tracking identifications, wherein the insufficient tracking strength indictor information is determined based, at least in part, on a previously captured image from each camera of the plurality of cameras; determining, based on the tracking data, a position and an orientation of the tracked object within a virtual three-dimensional coordinate system; and outputting the position and the orientation of the tracked object.

14. The method of claim 13, further comprising:
- determining tracking strength indicator information for each remaining image in the synchronized image captures; and
- utilizing each remaining image of the synchronized image captures that includes a tracking strength indicator that exceeds the predetermined threshold.

15. The method of claim 14, wherein determining the tracking strength indicator information includes determining how much of an aspect of the tracked object is occluded in each image of the synchronized image captures.

16. The method of claim 14, wherein:
- the tracked object includes a tracking frame with the plurality of infrared-reflective marker components; and
- determining how much of the aspect of the tracked object is occluded includes determining how many of the plurality of infrared-reflective marker components are visible in each image of the synchronized image captures.

17. The method of claim 14, further comprising a surgical robot configured to:
- receive the position and the orientation of the tracked object with a surgical robot; and with the surgical robot, actuating a surgical tool in response to the position and the orientation of the tracked object.

18. At least one non-transitory machine-readable medium including instructions for tracking an object within a surgical field, which when executed by a processor, cause the processor to:

receive synchronized image captures from a plurality of cameras in a mesh of cameras, wherein the plurality of cameras includes at least two pairs of at least three pairs of infrared cameras distributed around the surgical field in the mesh of cameras, wherein each pair of infrared cameras includes two infrared cameras fixedly positioned in a respective housing, the received synchronized image captures including a first set of images from a first pair of infrared cameras, a second set of images from a second pair of infrared cameras, and a third set of images from a third pair of infrared cameras, wherein at least a portion of the synchronized image captures include information indicative of a position and orientation of a tracked object within the surgical field, wherein the tracked object includes a plurality of infrared-reflective marker components arranged rigidly in a specified orientation to one another, the plurality of infrared-reflective marker components being attachable as a rigid structure to a surgical instrument or an anatomy of a patient;

analyze the synchronized image captures, including identifying tracking strength indicator information for each of the first set of images, the second set of images, and the third set of images and detecting that at least one of the synchronized image captures includes insufficient tracking strength indicator information, to generate tracking data for the tracked object using only data captured by cameras of the mesh of cameras, wherein the tracking data is generated from information extracted from at least two of the first set of images, the second set of images, and the third set of images, the at least two having sufficient tracking strength indicator information, that transgresses a predetermined threshold, wherein the pre-determined threshold is set to avoid false positive tracking identifications;

determine, based on the tracking data, a position and an orientation of the tracked object within a virtual three-dimensional coordinate system; and output the position and the orientation of the tracked object.

* * * * *